(12) United States Patent
Seliktar et al.

(10) Patent No.: US 9,120,872 B2
(45) Date of Patent: *Sep. 1, 2015

(54) MATRIX COMPOSED OF A NATURALLY-OCCURRING PROTEIN BACKBONE CROSS LINKED BY A SYNTHETIC POLYMER AND METHODS OF GENERATING AND USING SAME

(75) Inventors: Dror Seliktar, Haifa (IL); Liora Almany, Atlit (IL)

(73) Assignee: Regentis Biomaterials Ltd., Or-Akiva (IL)

( * ) Notice: Subject to any disclaimer, the term of this patent is extended or adjusted under 35 U.S.C. 154(b) by 1283 days.

This patent is subject to a terminal disclaimer.

(21) Appl. No.: 12/912,809

(22) Filed: Oct. 27, 2010

(65) Prior Publication Data

US 2011/0038828 A1    Feb. 17, 2011

Related U.S. Application Data

(60) Division of application No. 11/472,520, filed on Jun. 22, 2006, now Pat. No. 7,842,667, which is a continuation-in-part of application No. PCT/IL2004/001136, filed on Dec. 15, 2004.

(60) Provisional application No. 60/530,917, filed on Dec. 22, 2003.

(51) Int. Cl.
| | |
|---|---|
| C07K 14/75 | (2006.01) |
| A61K 47/48 | (2006.01) |
| A61L 24/10 | (2006.01) |
| A61L 27/18 | (2006.01) |
| A61L 27/22 | (2006.01) |
| A61L 27/24 | (2006.01) |
| A61L 27/38 | (2006.01) |
| A61L 27/52 | (2006.01) |
| C12N 5/00 | (2006.01) |
| A61K 38/00 | (2006.01) |

(52) U.S. Cl.
CPC ........... *C07K 14/75* (2013.01); *A61K 47/48215* (2013.01); *A61K 47/48292* (2013.01); *A61K 47/48784* (2013.01); *A61L 24/106* (2013.01); *A61L 27/18* (2013.01); *A61L 27/225* (2013.01); *A61L 27/227* (2013.01); *A61L 27/24* (2013.01); *A61L 27/38* (2013.01); *A61L 27/52* (2013.01); *C12N 5/0068* (2013.01); *A61K 38/00* (2013.01); *C12N 2533/30* (2013.01); *C12N 2533/40* (2013.01); *C12N 2533/50* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | |
|---|---|---|
| 4,069,216 A | 1/1978 | Shanbrom |
| 4,188,318 A | 2/1980 | Shanbrom |
| 4,925,924 A | 5/1990 | Silver et al. |
| 4,970,298 A | 11/1990 | Silver et al. |
| 5,410,016 A | 4/1995 | Hubbell et al. |
| 5,529,914 A | 6/1996 | Hubbell et al. |
| 5,567,435 A | 10/1996 | Hubbell et al. |
| 5,573,934 A | 11/1996 | Hubbell et al. |
| 5,614,587 A | 3/1997 | Rhee et al. |
| 5,626,863 A | 5/1997 | Hubbell et al. |
| 5,733,563 A | 3/1998 | Fortier |
| 5,834,274 A | 11/1998 | Hubbell et al. |
| 5,843,743 A | 12/1998 | Hubbell et al. |
| 5,858,746 A | 1/1999 | Hubbell et al. |
| 5,863,984 A | 1/1999 | Doillon et al. |
| 5,902,599 A | 5/1999 | Anseth et al. |
| 5,986,043 A | 11/1999 | Hubbell et al. |
| 6,060,582 A | 5/2000 | Hubbell et al. |
| 6,129,761 A | 10/2000 | Hubbell |
| 6,153,211 A | 11/2000 | Hubbell et al. |
| 6,224,893 B1 | 5/2001 | Langer et al. |
| 6,306,922 B1 | 10/2001 | Hubbell et al. |
| 6,403,672 B1 | 6/2002 | Randolph et al. |
| 6,565,842 B1 | 5/2003 | Sojomihardjo et al. |
| 6,703,037 B1 | 3/2004 | Hubbell et al. |
| 6,858,229 B1 | 2/2005 | Hubbell et al. |
| 6,864,301 B2 | 3/2005 | Randolph et al. |
| 6,911,227 B2 | 6/2005 | Hubbell et al. |
| 7,842,667 B2 | 11/2010 | Seliktar et al. |
| 8,007,774 B2 * | 8/2011 | Seliktar et al. ............... 424/78.2 |
| 8,846,020 B2 * | 9/2014 | Seliktar et al. ............. 424/78.17 |
| 2004/0082511 A1 | 4/2004 | Watzek et al. |

(Continued)

FOREIGN PATENT DOCUMENTS

| | | |
|---|---|---|
| EP | 0605797 | 7/1994 |
| EP | 0680990 | 11/1995 |

(Continued)

OTHER PUBLICATIONS

Notice of Allowance Dated Apr. 11, 2011 From the US Patent and Trademark Office Re.: U.S. Appl. No. 11/472,437.

(Continued)

*Primary Examiner* — Anand Desai

(57) ABSTRACT

A method of treating a disorder characterized by tissue damage is provided. The method comprising providing to a subject in need-thereof a composition which comprises a synthetic polymer attached to denatured fibrinogen or a therapeutic portion of the fibrinogen, the composition being formulated for releasing the therapeutic portion of the fibrinogen in a pharmacokinetically regulated manner, thereby treating the disorder characterized by tissue damage or malformation.

16 Claims, 26 Drawing Sheets

(18 of 26 Drawing Sheet(s) Filed in Color)

(56) References Cited

U.S. PATENT DOCUMENTS

| | | | |
|---|---|---|---|
| 2006/0233854 A1 | 10/2006 | Seliktar et al. | |
| 2006/0233855 A1 | 10/2006 | Seliktar et al. | |
| 2012/0020911 A1 | 1/2012 | Seliktar et al. | |
| 2015/0030580 A1 | 1/2015 | Seliktar et al. | |

FOREIGN PATENT DOCUMENTS

| | | |
|---|---|---|
| EP | 0976759 | 2/2000 |
| WO | WO 98/32466 | 7/1998 |
| WO | WO 99/34833 | 7/1999 |
| WO | WO 01/53324 | 7/2001 |
| WO | WO 02/18441 | 3/2002 |
| WO | WO 2004/041298 | 5/2004 |
| WO | WO 2005/061018 | 7/2005 |
| WO | WO 2008/126092 | 10/2008 |

OTHER PUBLICATIONS

European Search Report and the European Search Opinion Dated May 20, 2011 From the European Patent Office Re. Application No. 10012382.7.
Official Action Dated Aug. 15, 2013 From the US Patent and Trademark Office Re. U.S. Appl. No. 13/181,562.
Almany et al. "Biosynthetic Hydrogel Scaffolds Made From Fibrinogen and Polyethylene Glycol for 3D Cell Cultures", Biomaterials, 26: 2467-2477, 2005.
Invitation Pursuant to Article 94(3) and Rule 71(1) EPC Dated May 19, 2011 From the European Patent Office Re. Application No. 04806668.2.
Response Dated Jul. 29, 2011 to Invitation Pursuant to Article 94(3) and Rule 71(1) EPC of May 19, 2011 From the European Patent Office Re. Application No. 04806668.2.
Communication Pursuant to Article 94(3) EPC Dated Dec. 2, 2010 From the European Patent Office Re. Application No. 04806668.2.
Response Dated Mar. 4, 2011 to Communication Pursuant to Article 94(3) EPC of Dec. 2, 2010 From the European Patent Office Re. Application No. 04806668.2.
Communication Pursuant to Rules 70(2) and 70a(2) EPC and Reference to Rule 39(1) EPC Dated Jun. 28, 2011 From the European Patent Office Re. Application No. 10012382.7.
Response Dated Oct. 28, 2010 to Official Action of Jun. 29, 2010 From the US Patent and Trademark Office Re.: U.S. Appl. No. 11/472,437.
Final Official Action Dated Feb. 26, 2014 From the US Patent and Trademark Office Re.: U.S. Appl. No. 13/181,562.
Communication Pursuant to Article 94(3) EPC Dated Apr. 2, 2012 From the European Patent Office Re. Application No. 10012382.7.
Notice of Allowance Dated Jun. 4, 2014 From the US Patent and Trademark Office Re. U.S. Appl. No. 13/181,562.
International Preliminary Report on Patentability Dated Jul. 6, 2006 From the International Bureau of WIPO Re.: Application No. PCT/IL2004/001136.
International Search Report Dated Aug. 2, 2005 From the International Searching Authority Re.: Application No. PCT/IL2004/001136.
Official Action Dated Oct. 4, 2007 From the US Patent and Trademark Office Re.: U.S. Appl. No. 11/472,520.
Official Action Dated Jan. 8, 2009 From the US Patent and Trademark Office Re.: U.S. Appl. No. 11/472,437.
Official Action Dated Apr. 28, 2008 From the US Patent and Trademark Office Re.: U.S. Appl. No. 11/472,437.
Communication Pursuant to Article 94(3) EPC Dated Jan. 5, 2009 From the European Patent Office Re.: Application No. 04806668.2.
Communication Pursuant to Article 94(3) EPC Dated Jul. 6, 2009 From the European Patent Office Re.: Application No. 04806668.2.
Communication Pursuant to Article 94(3) EPC Dated Jul. 25, 2008 From the European Patent Office Re.: Application No. 07110777.5.
Communication Pursuant to Article 96(2) EPC Dated Dec. 11, 2006 From the European Patent Office Re.: Application No. 04806668.2.
European Search Report Dated Oct. 22, 2007 From the European Patent Office Re.: Application No. 07110777.5.
International Search Report Dated Jun. 1, 2005 From the International Searching Authority Re.: Application No. PCT/IL2004/001136.
Interview Summary Dated Oct. 18, 2010 From the US Patent and Trademark Office Re.: U.S. Appl. No. 11/472,437.
Invitation Pursuant to Article 94(3) and Rule 71(1) EPC Dated Jun. 10, 2010 From the European Patent Office Re. Application No. 04806668.2.
Notice of Allowance Dated Jul. 26, 2010 From the US Patent and Trademark Office Re.: U.S. Appl. No. 11/472,520.
Official Action Dated Feb. 4, 2010 From the US Patent and Trademark Office Re.: U.S. Appl. No. 11/472,520.
Official Action Dated Aug. 7, 2008 From the US Patent and Trademark Office Re.: U.S. Appl. No. 11/472,437.
Official Action Dated Nov. 12, 2008 From the US Patent and Trademark Office Re.: U.S. Appl. No. 11/472,520.
Official Action Dated Jun. 15, 2007 From the US Patent and Trademark Office Re.: U.S. Appl. No. 11/472,520.
Official Action Dated Sep. 17, 2009 From the US Patent and Trademark Office Re.: U.S. Appl. No. 11/472,437.
Official Action Dated Jan. 21, 2010 From the US Patent and Trademark Office Re.: U.S. Appl. No. 11/472,437.
Official Action Dated Jul. 22, 2009 From the US Patent and Trademark Office Re.: U.S. Appl. No. 11/472,520.
Official Action Dated Jun. 29, 2010 From the US Patent and Trademark Office Re.: U.S. Appl. No. 11/472,437.
Response Dated May 3, 2010 to Official Action of Feb. 4, 2010 From the US Patent and Trademark Office Re.: U.S. Appl. No. 11/472,520.
Response Dated Dec. 16, 2009 to Official Action of Sep. 17, 2009 From the US Patent and Trademark Office Re.: U.S. Appl. No. 11/472,437.
Response Dated Oct. 18, 2010 to Invitation Pursuant to Article 94(3) and Rule 71(1) EPC of Jun. 10, 2010 From the European Patent Office Re. Application No. 04806668.2.
Response Dated Oct. 19, 2009 to Official Action of Jul. 22, 2009 From the US Patent and Trademark Office Re.: U.S. Appl. No. 11/472,520.
Response Dated Apr. 21, 2010 to Official Action of Jan. 21, 2010 From the US Patent and Trademark Office Re.: U.S. Appl. No. 11/472,437.
Response Dated Jan. 28, 2010 to Communication Pursuant to Article 94(3) EPC of Jul. 6, 2009 From the European Patent Office Re.: Application No. 04806668.2.
Written Opinion Dated Jun. 1, 2005 From the International Searching Authority Re.: Application No. PCT/IL2004/001136.
Almany et al. "Biosynthetic Hydrogel Scaffolds Made From Fibrinogen and Polyethylene Glycol for 3D Cell Cultures", Biomaterials, XP004673411, 26(15): 2467-2477, May 15, 2005. § [03.5], [0004], p. 2471, Table 1.
Deible et al. "Molecular Barriers to Biomaterial Thrombosis by Modification of Surface Proteins With Polyethylene Glycol", Biomaterials, 19: 1885-1893, 1998.
Dikovsky et al. "The Effect of Structural Alterations of PEG-Fibrinogen Hydrogel Scaffolds on 3-D Cellular Morphology and Cellular Migration", Biomaterials, XP005193217, 27(8): 1496-1506, Oct. 21, 2005. Abstract, p. 1497, § 2.1, 2.2.
D'Urso et al. "Poly(Ethylene Glycol)-Serum Albumin Hydrogel as Matrix for Enzyme Immobilization: Biomedical Applications", Art. Cells, Blood Subs., and Biotech., 23(5): 587-595, 1995.
Gayet et al. "Drug Release From New Bioartificial Hydrogel", Art. Cells, Blood Subs., and Immob Biotech., 23(5): 605-611, 1995.
Halstenberg et al. "Biologically Engineered Protein-Graft-Poly(Ethylene Glycol) Hydrogels: A Cell Adhesive and Plasmin-Degradable Biosynthetic Material for Tissue Repair", Biomacromolecules, XP002454079, 3(4): 710-723, Jul. 2002. Abstract, p. 713, col. 2, § 3-p. 714, col. 1, § 2.
Hooftman et al. "Review: Poly(Ethylene Glycol)s With Reactive Endgroups. II. Practical Consideratiion for the Preparation of Protein-PEG Conjugates", Journal of Bioactive and Compatible Polymers, 11: 135-159, 1996.

(56) References Cited

OTHER PUBLICATIONS

Li et al. "Synthesis of Polyethylene Glycol (PEG) Derivatives and PEGylated-Peptide Biopolymer Conjugates", Biomacromolecules, 4: 1055-1067, 2003.
Meyers et al. "A Fibrin Adhesive Seal for the Repair of Osteochondral Fracture Fragments", Clinical Orthopaedics and Related Research, 182: 258-263, Jan.-Feb. 1984.
Pflüger et al. "Untersuchungen über das Einwachsen von Knochengewebe in poröse Metallimplantate", Wiener Klinische Wochenschrift, 91(14): 482-487, Jul. 13, 1979. & Translation Into English.
Seliktar et al. "MMP-2 Sensitive, VEGF-Bearing Bioactive Hydrogels for Promotion of Vascular Healing", Journal of Biomedical Materials Research, Part. A, 68(4): 704-716, 2004.
Veronese "Peptide and Protein PEGylation: A Review of Problems and Solutions", Biomaterials, 22: 405-417, 2001.
Wells "Additivity of Mutational Effects in Proteins", Perspectives in Biochemistry, Biochemistry, 29(37): 8509-8517, Sep. 18, 1990.
Zalipsky "Chemistry of Polyethylene Glycol Conjugates With Biologically Active Molecules", Advanced Drug Delivery Reviews, 16: 157-182, 1995.
Summons to Attend Oral Proceedings Pursuant to Rule 115(1) EPC Dated Jan. 28, 2013 From the European Patent Office Re. Application No. 07110777.5.
Response Dated Apr. 4, 2011 to Official Action of Jan. 3, 2011 From the US Patent and Trademark Office Re.: U.S. Appl. No. 11/472,437.
Restriction Official Action Dated Mar. 12, 2013 From the US Patent and Trademark Office Re. U.S. Appl. No. 13/181,562.
Communication Under Rule 71(3) EPC Dated Nov. 2, 2011 From the European Patent Office Re.: Application No. 04806668.2.
Official Action Dated Jan. 3, 2011 From the US Patent and Trademark Office Re.: U.S. Appl. No. 11/472,437.
Restriction Official Action Dated Mar. 13, 2015 From the US Patent and Trademark Office Re. U.S. Appl. No. 14/512,525.
Communication Pursuant to Article 94(3) EPC Dated Feb. 10, 2015 From the European Patent Office Re. Application No. 10012382.7.

\* cited by examiner

PEGylated Whole Fibrinogen

PEGylated Cleaved Fibrinogen

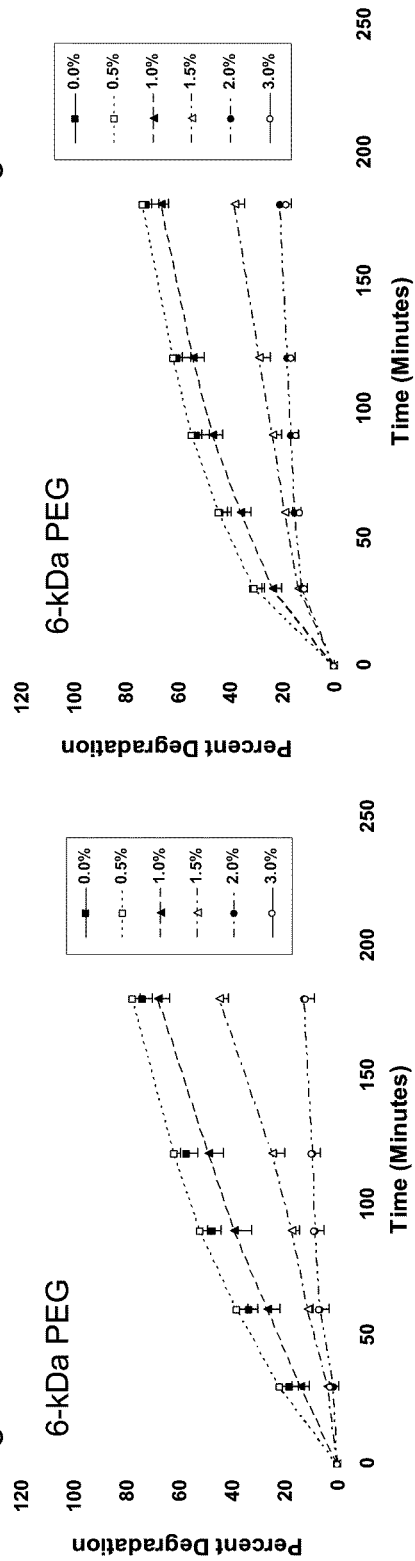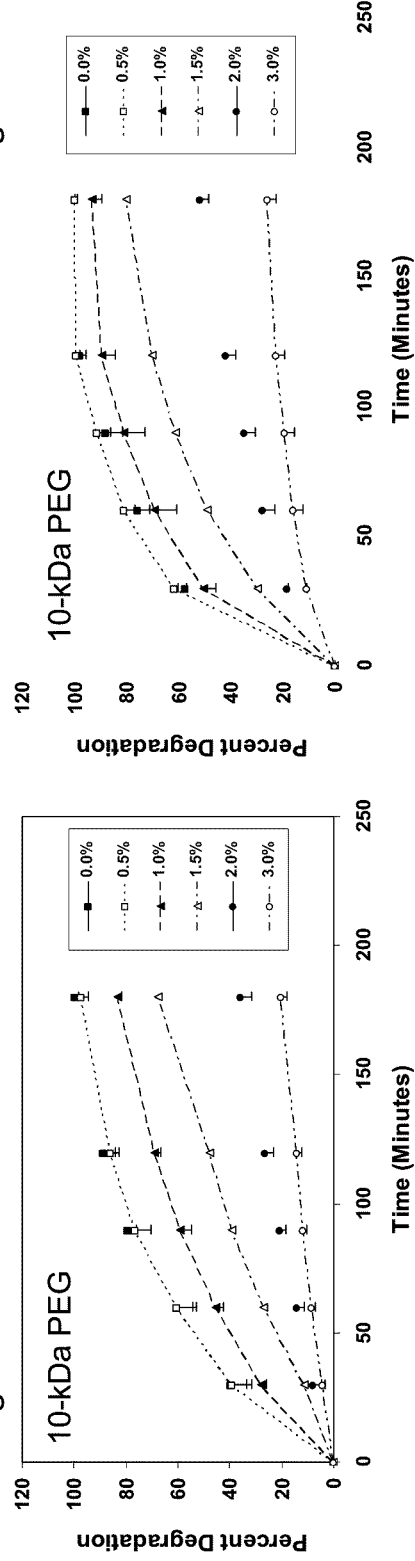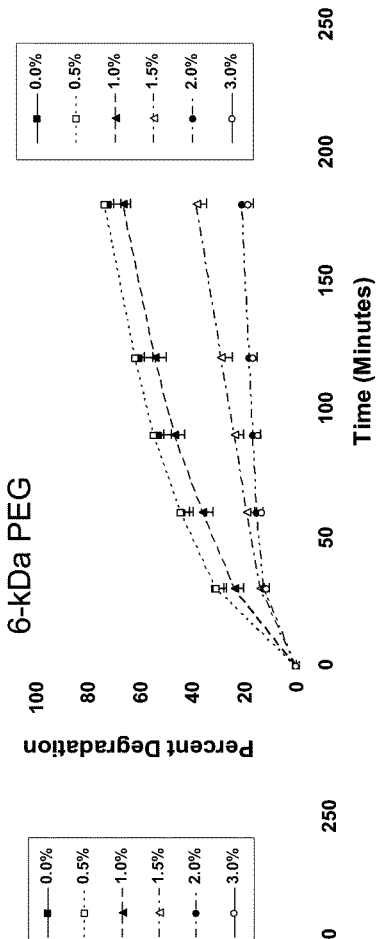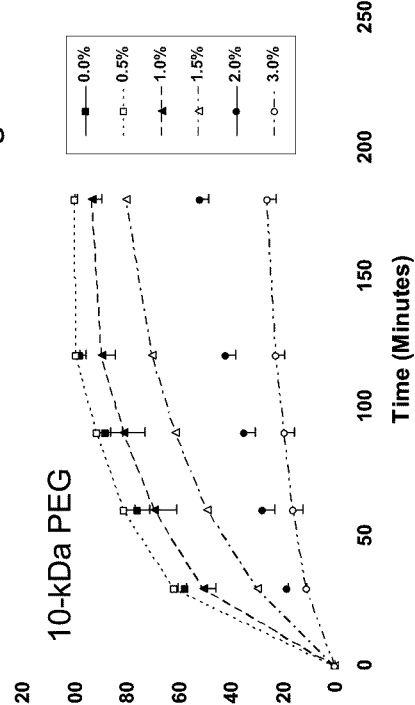

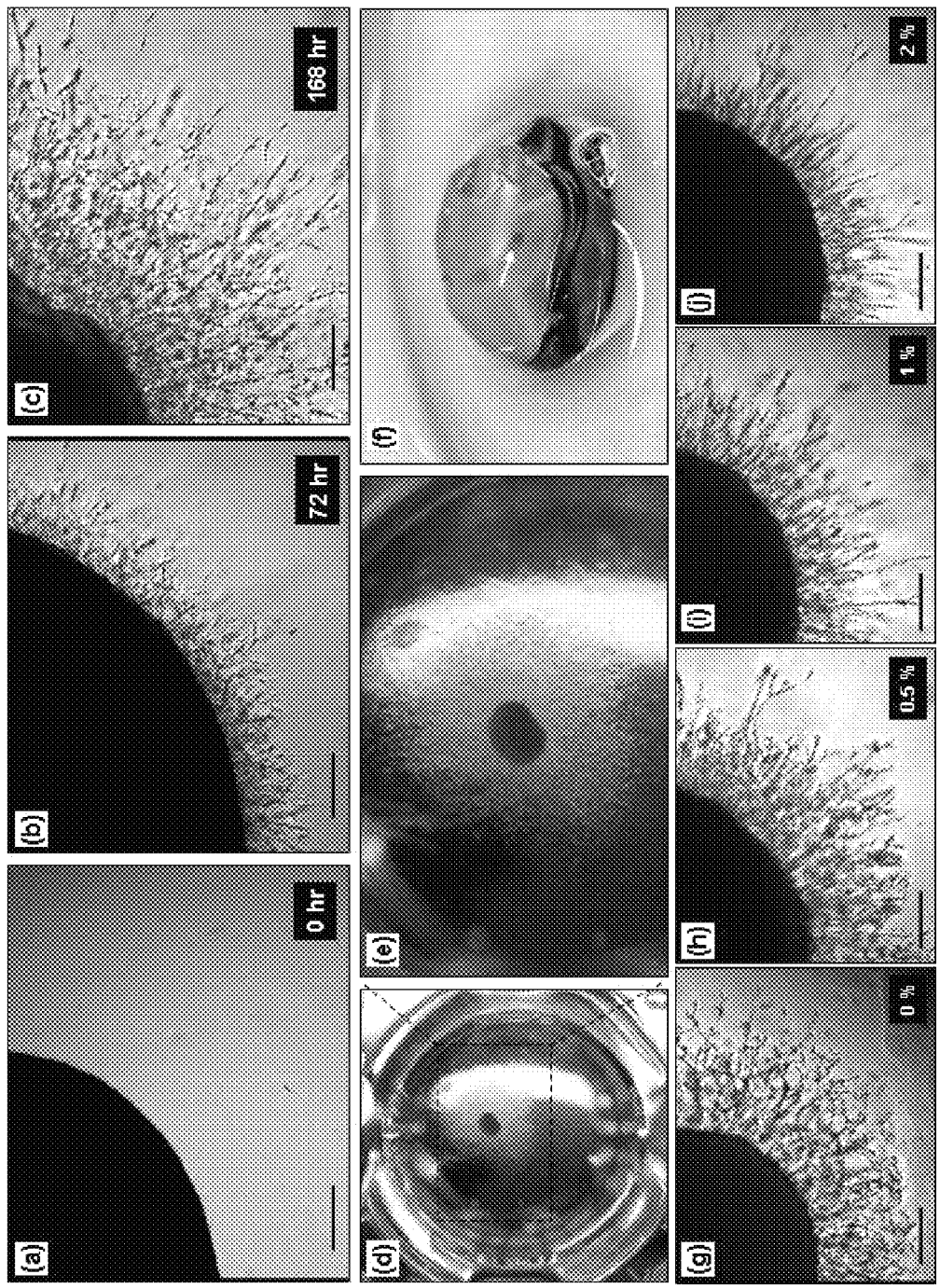
Figs. 6a-j

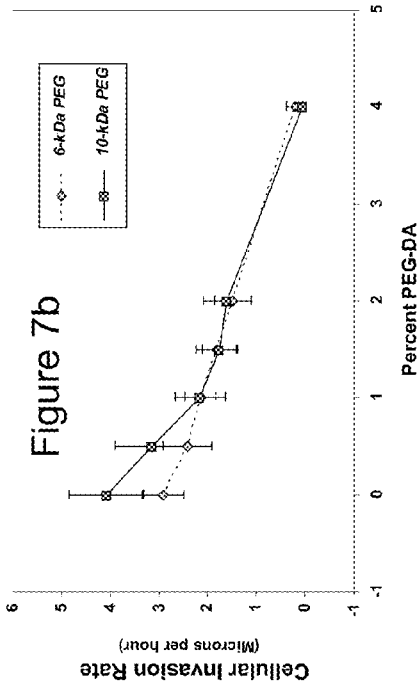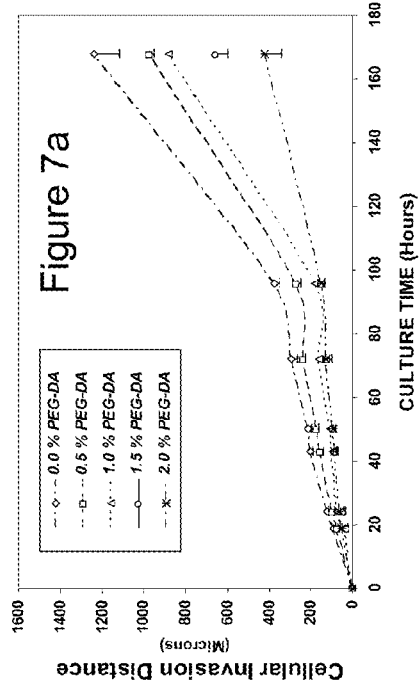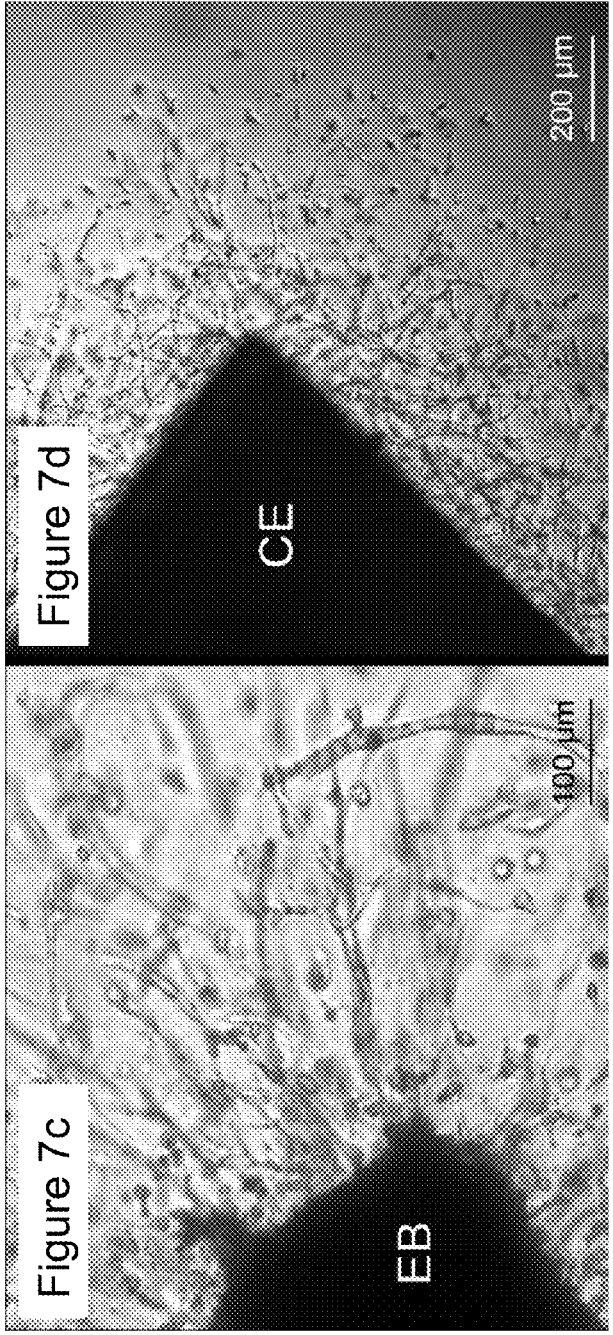

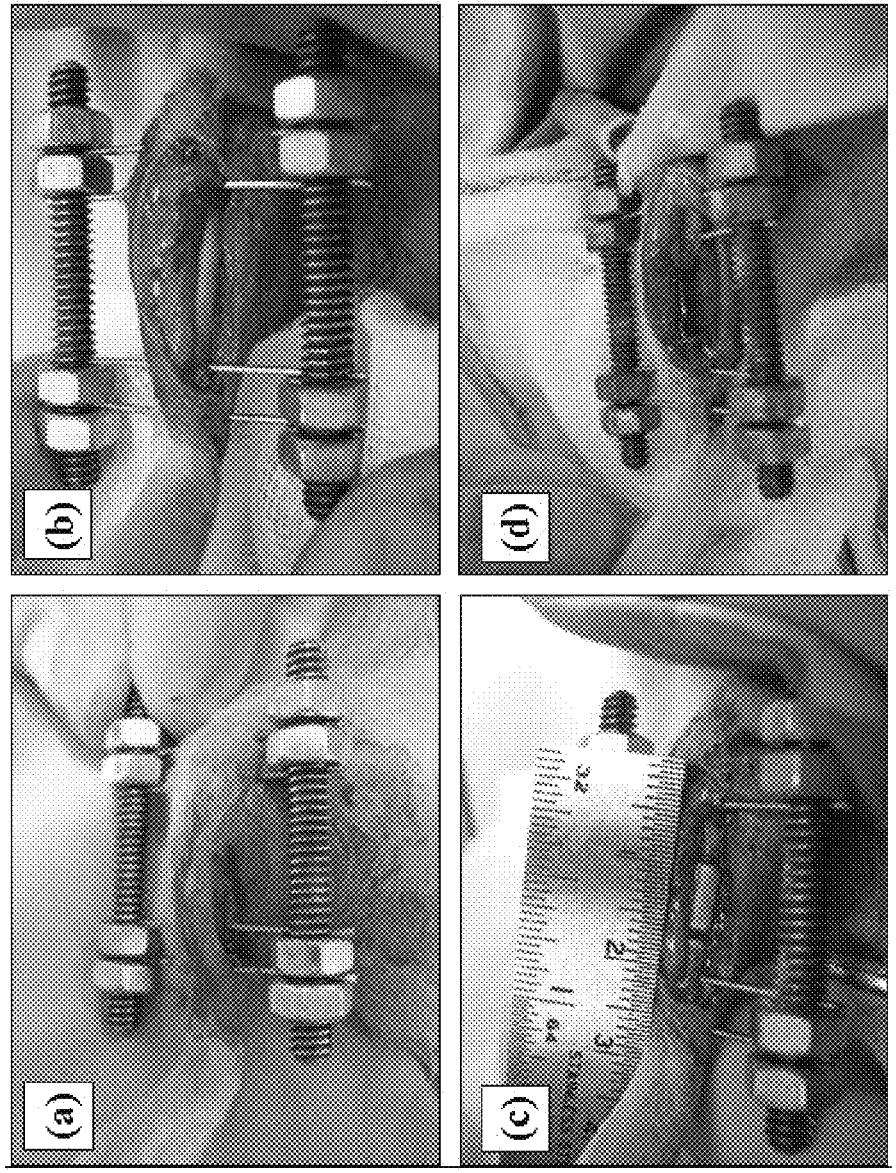
Figs. 8a-d

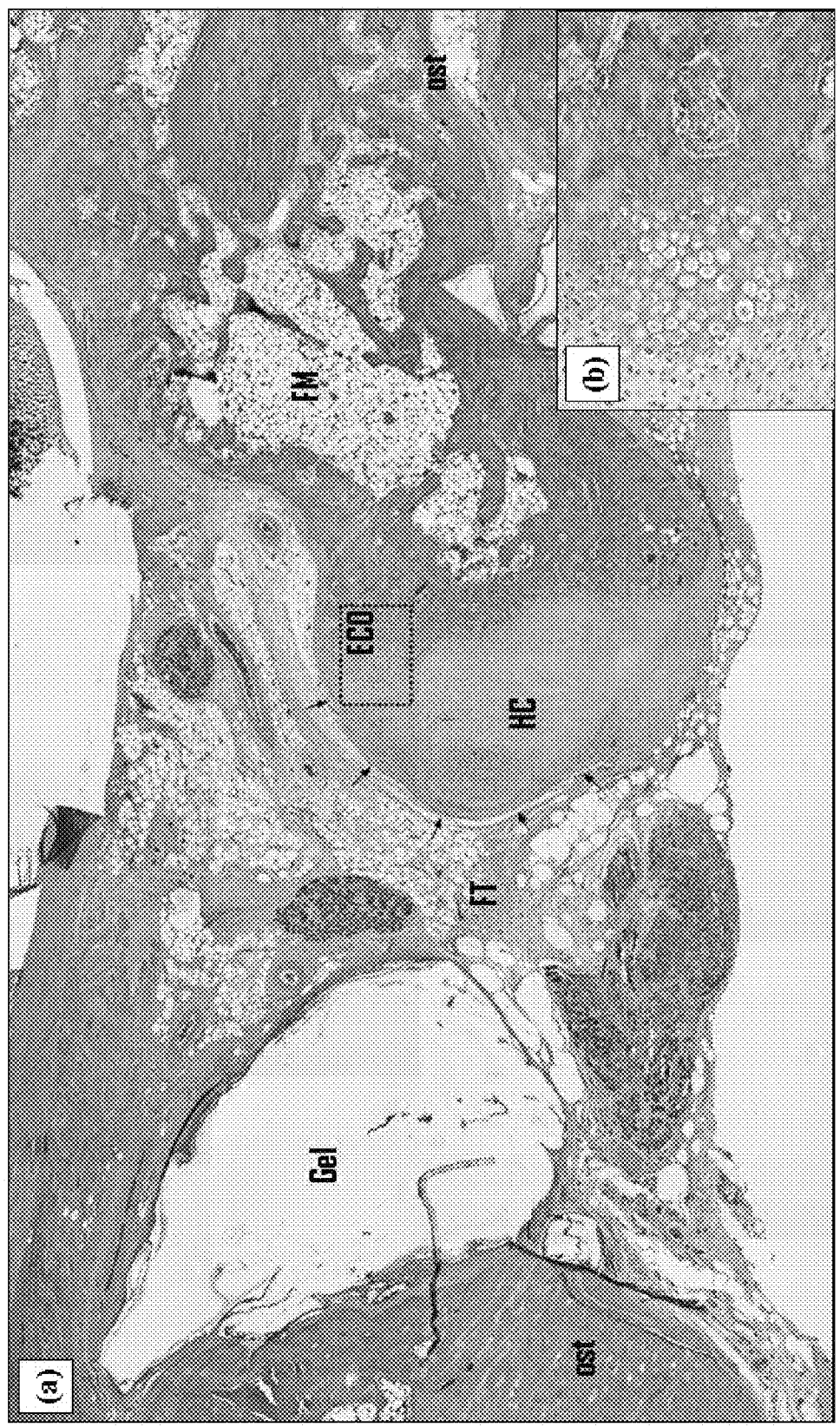
Figs. 10a-b

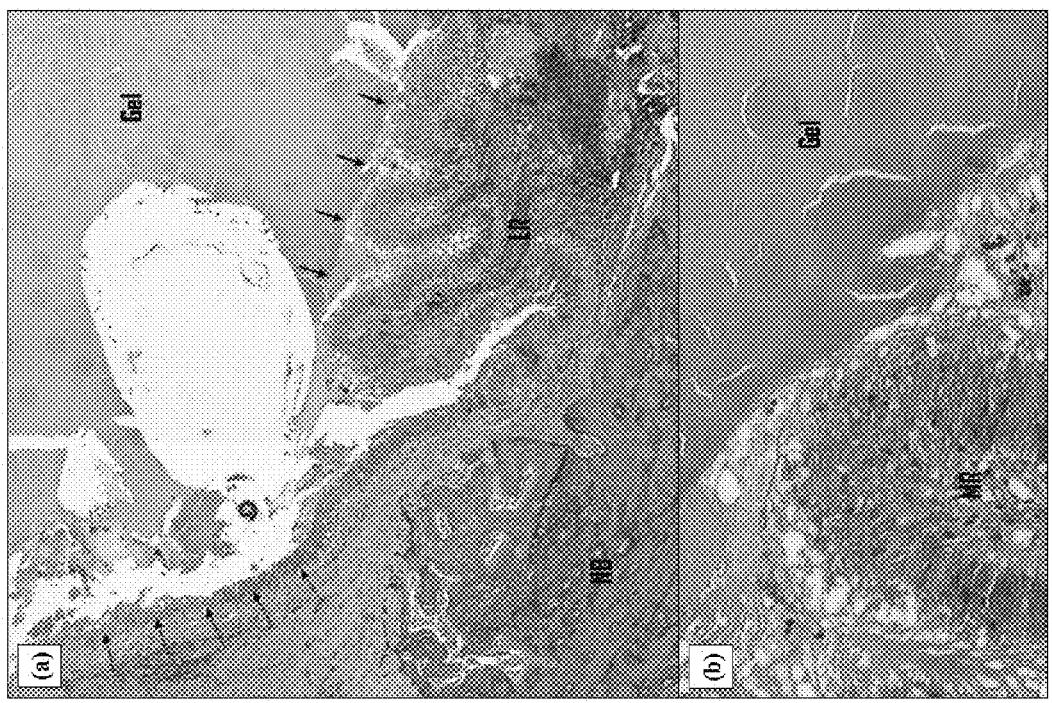
Figs. 11a-b

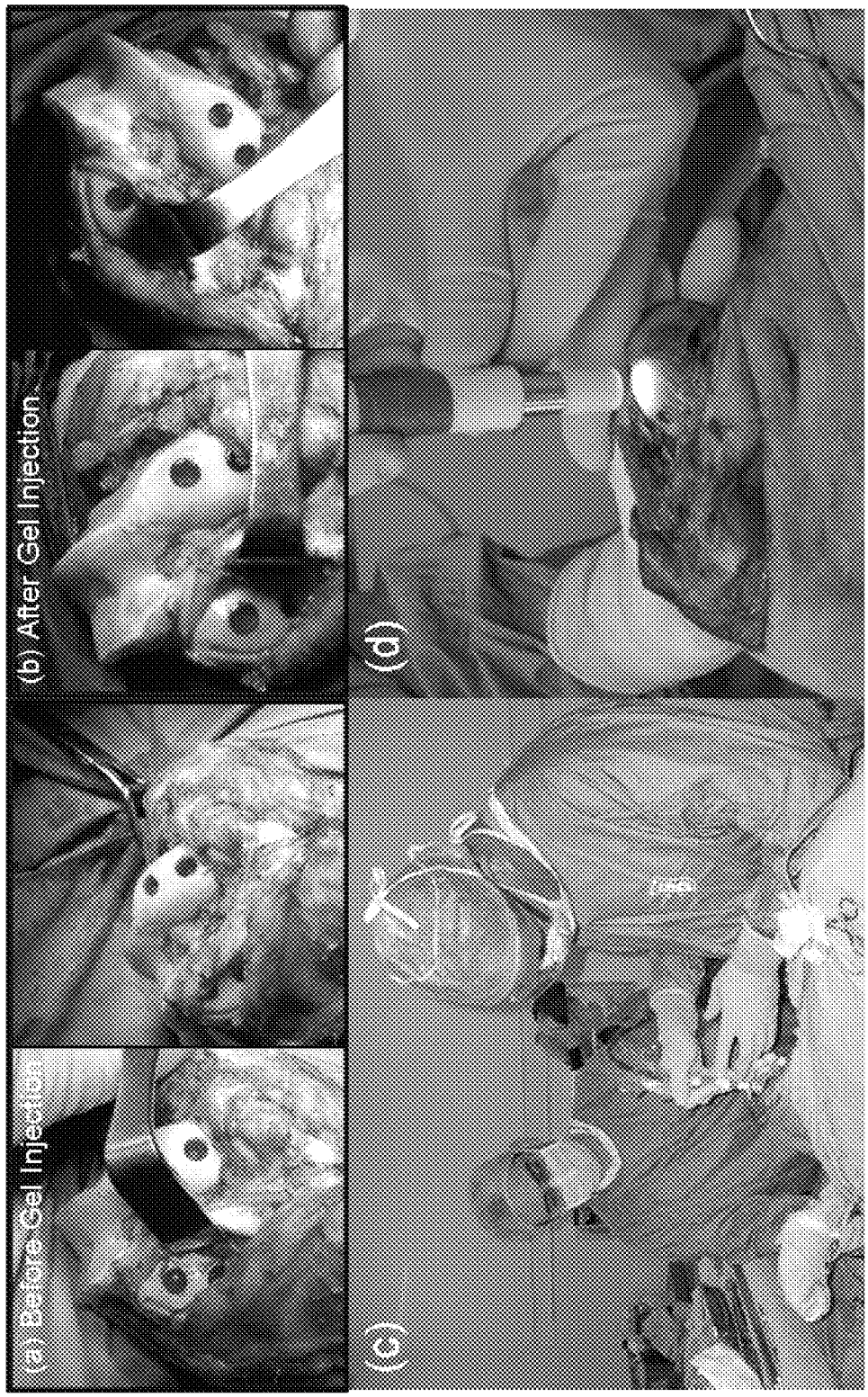
Figs. 12a-d

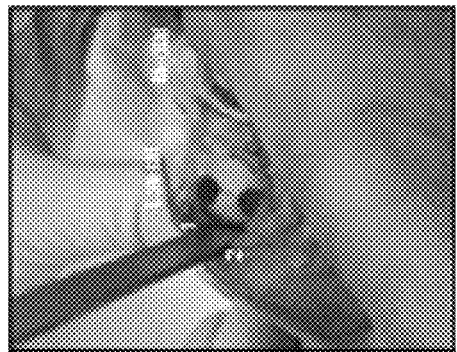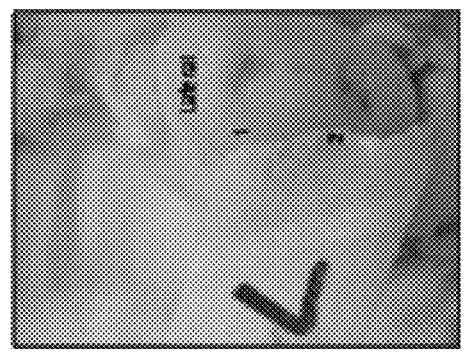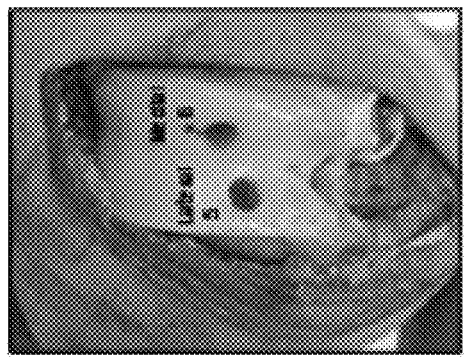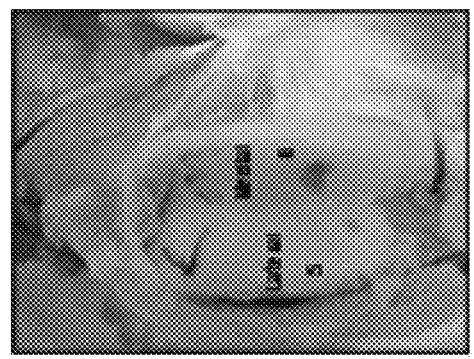
Figs. 13a-d

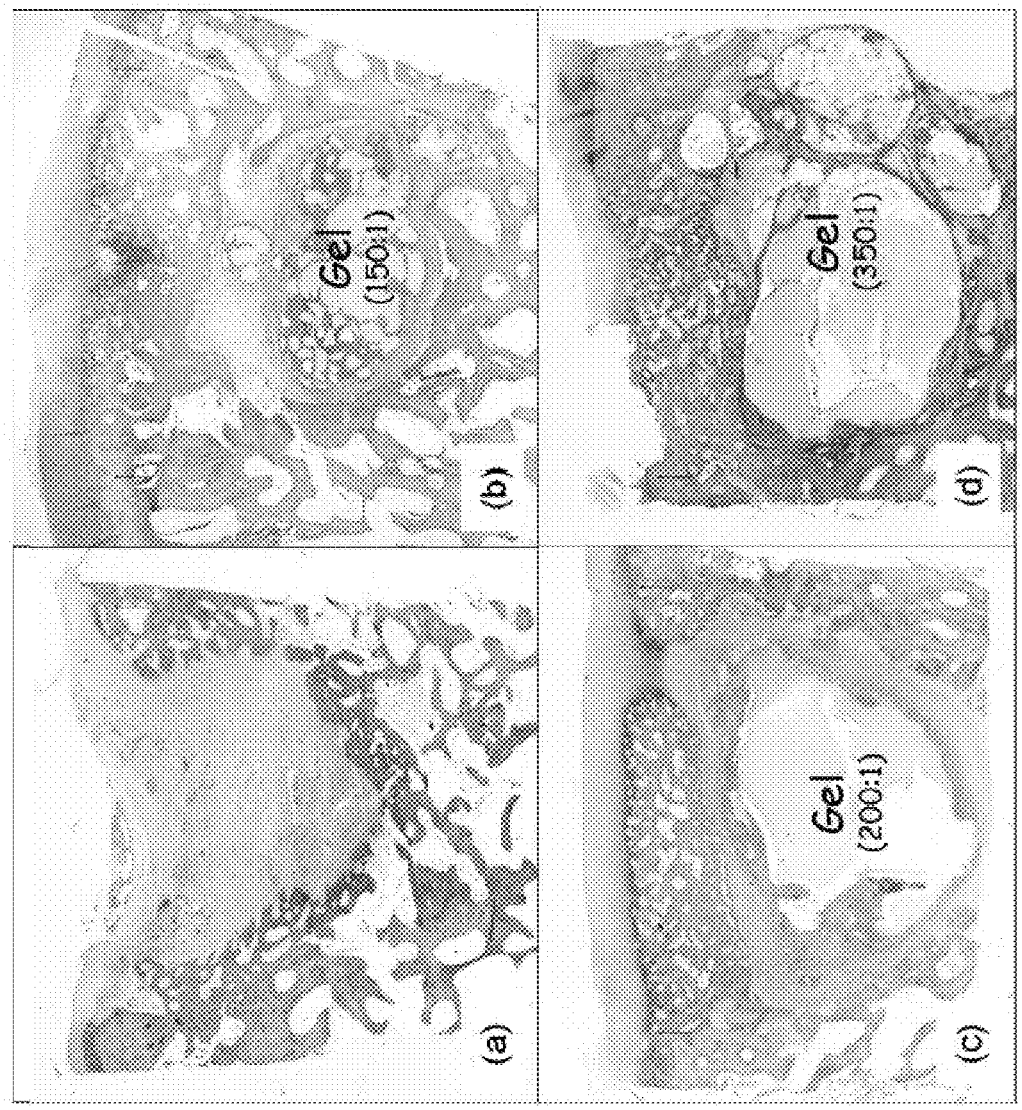
Figs. 14a-d

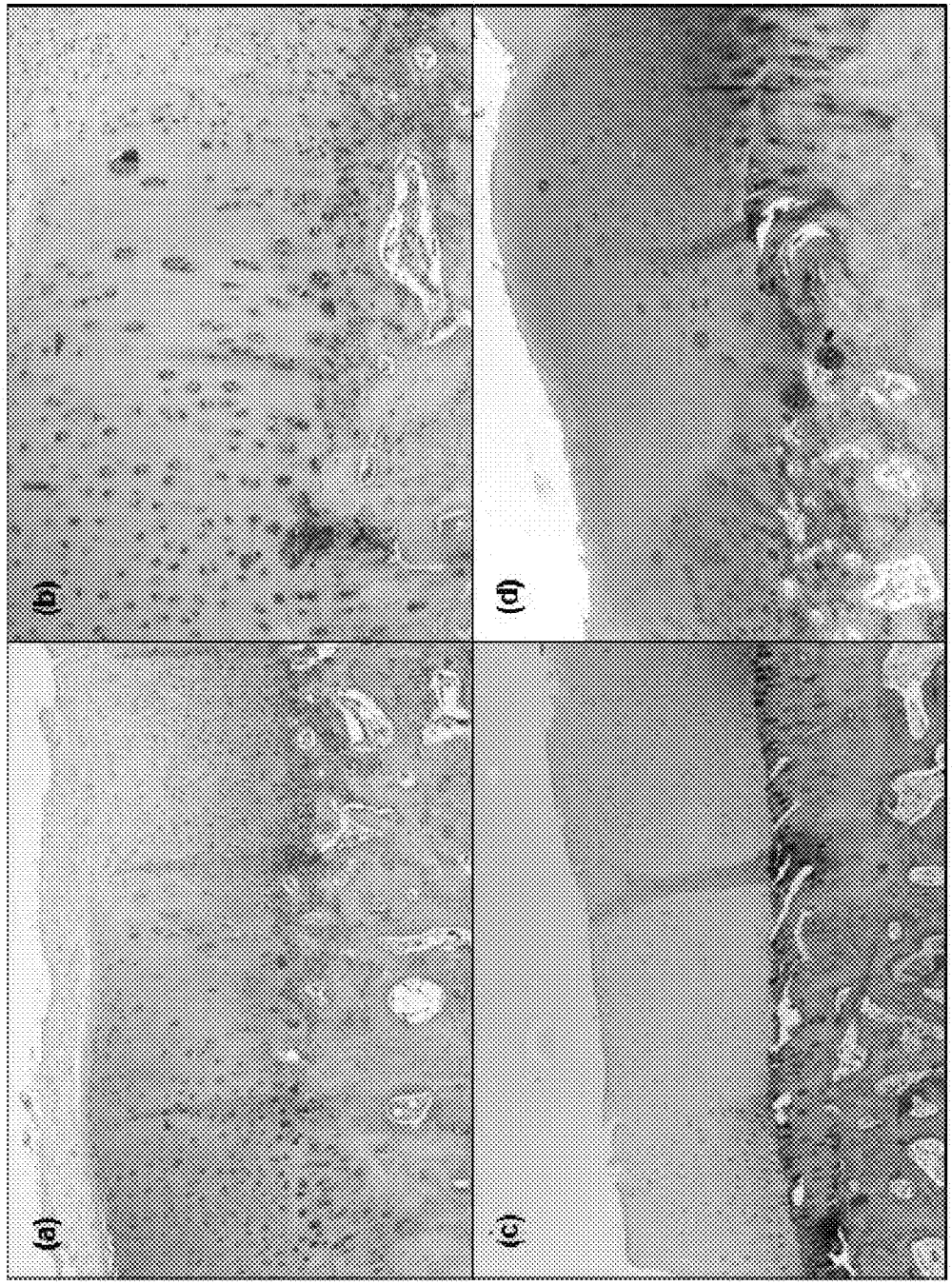
Figs. 19a-d

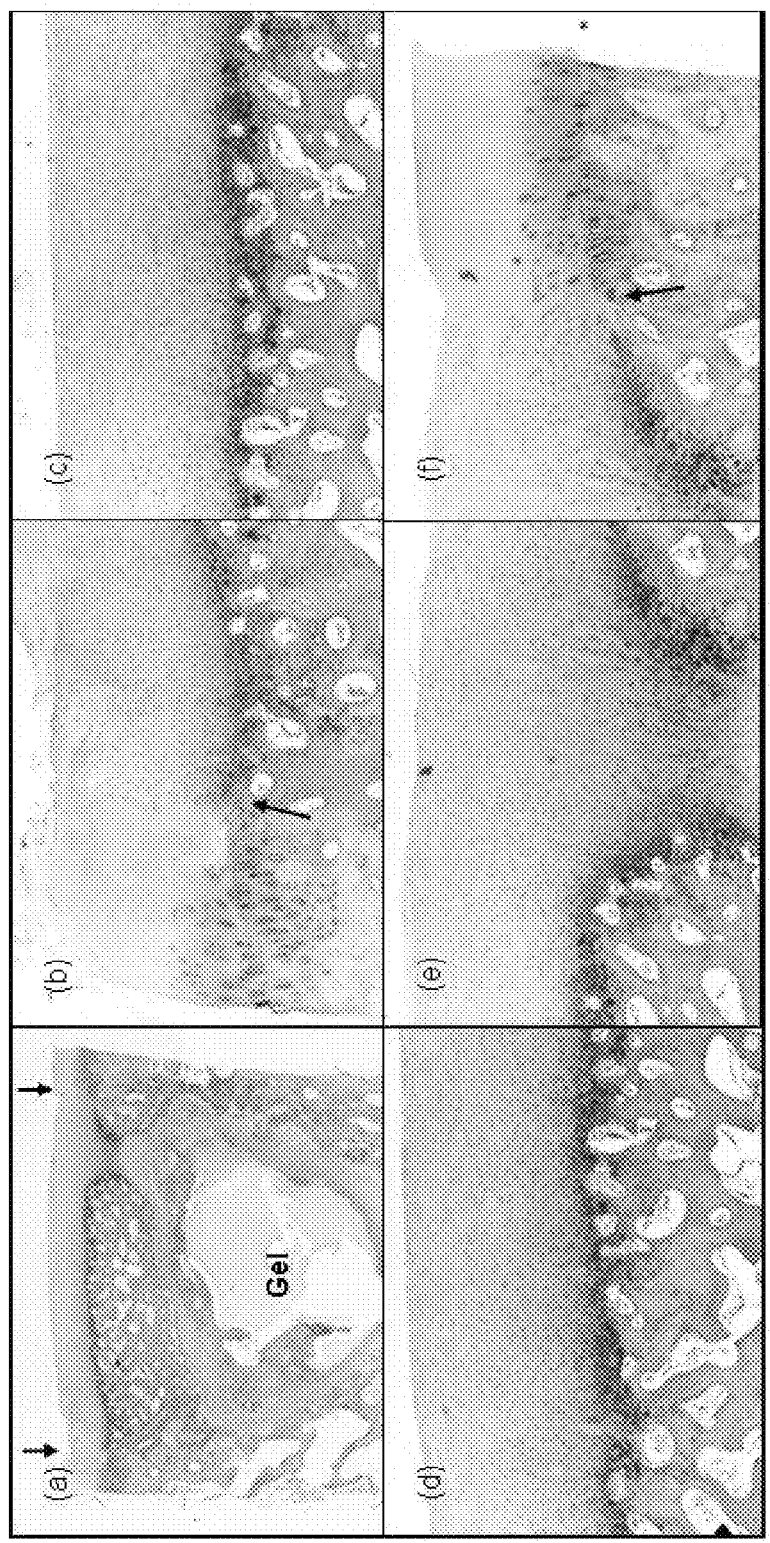
Figs. 20a-f

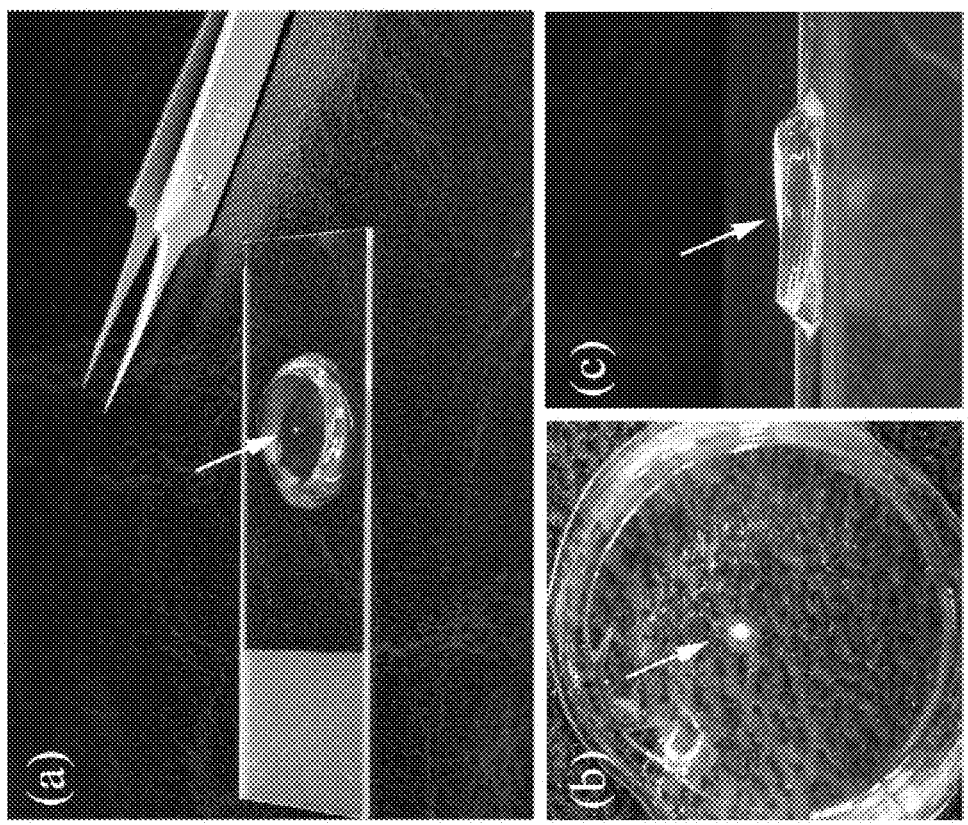
Figs. 21a-c

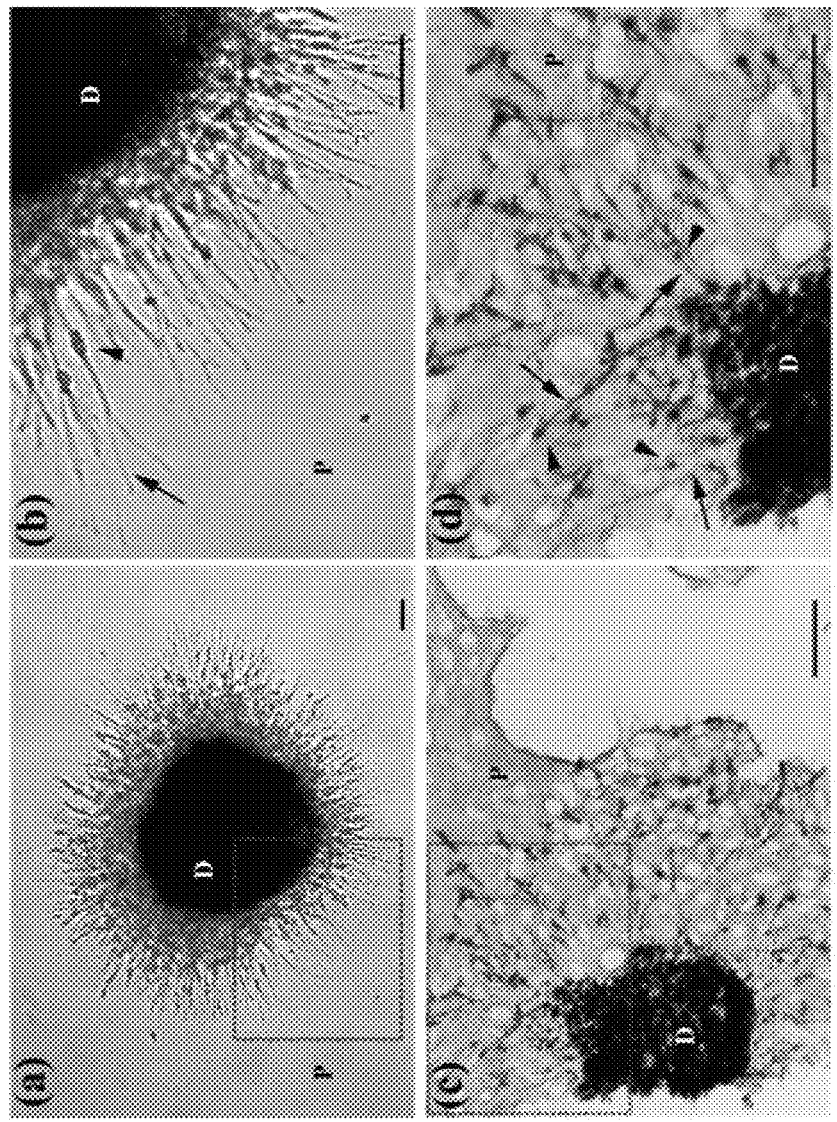
FIGs. 22a-d

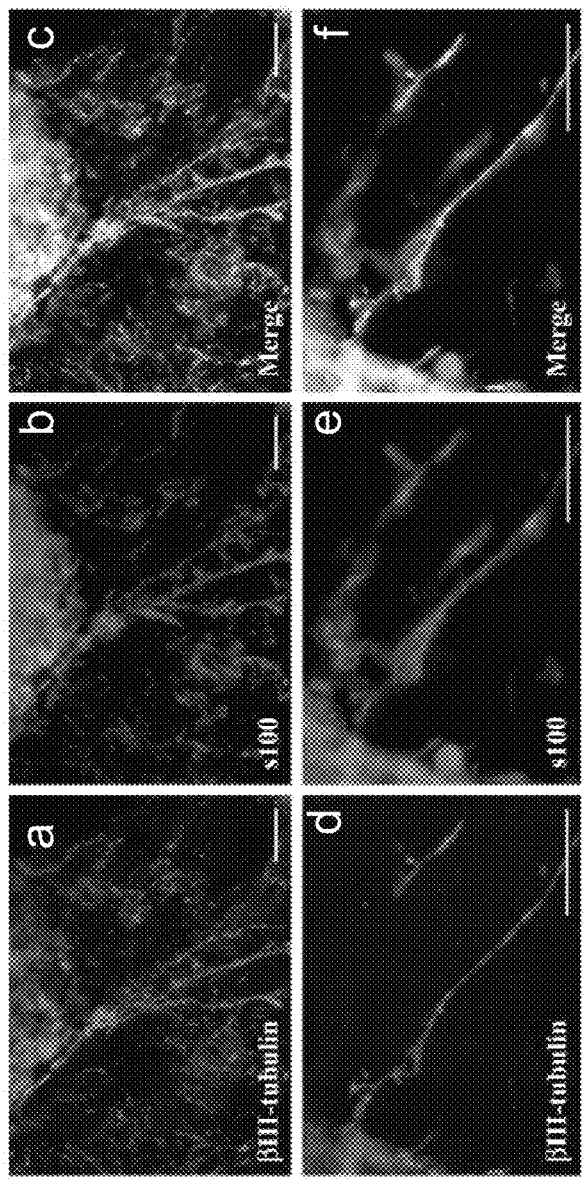
Figs. 23a-f

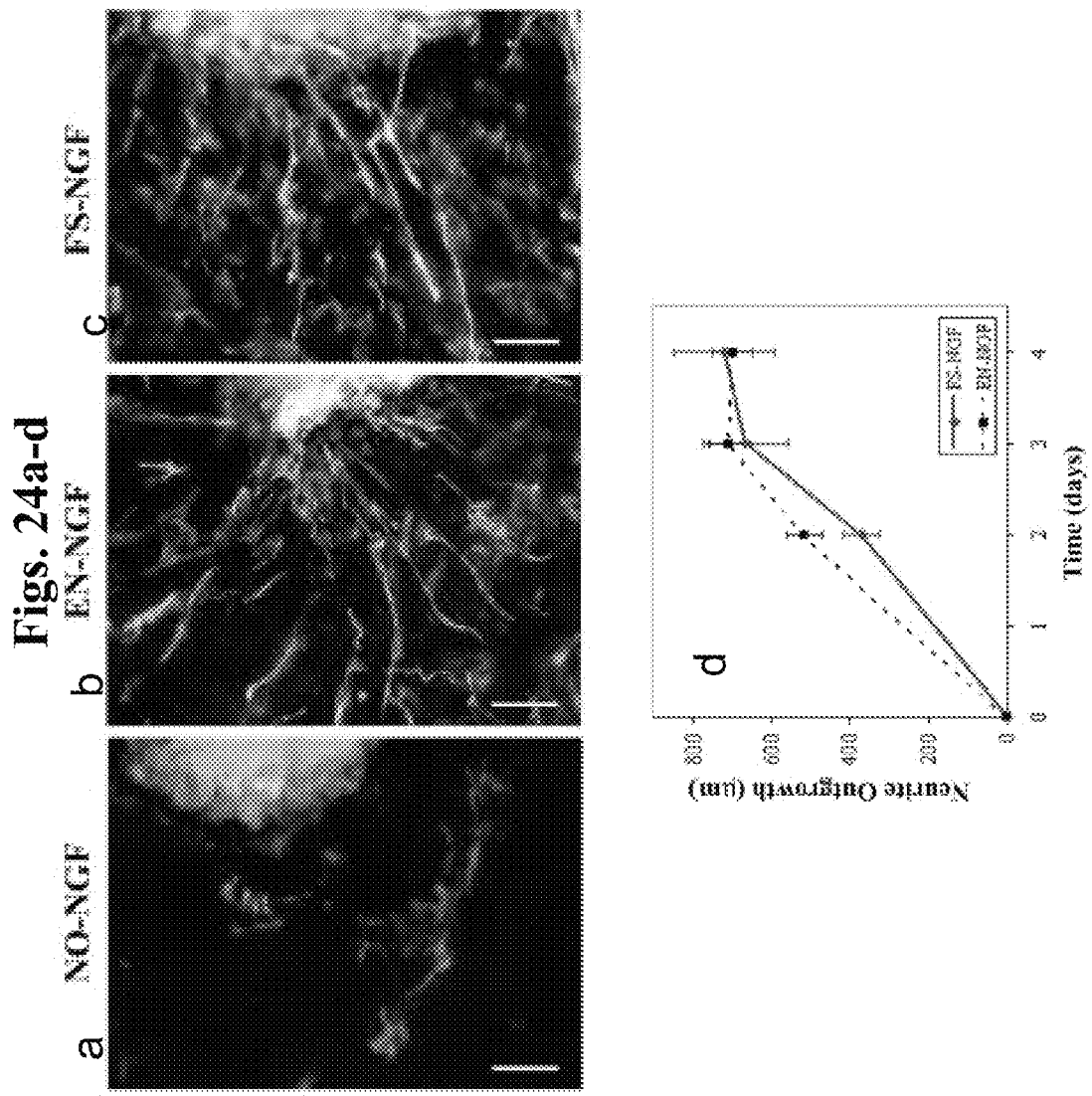
Figs. 24a-d

FIGs. 25a-u
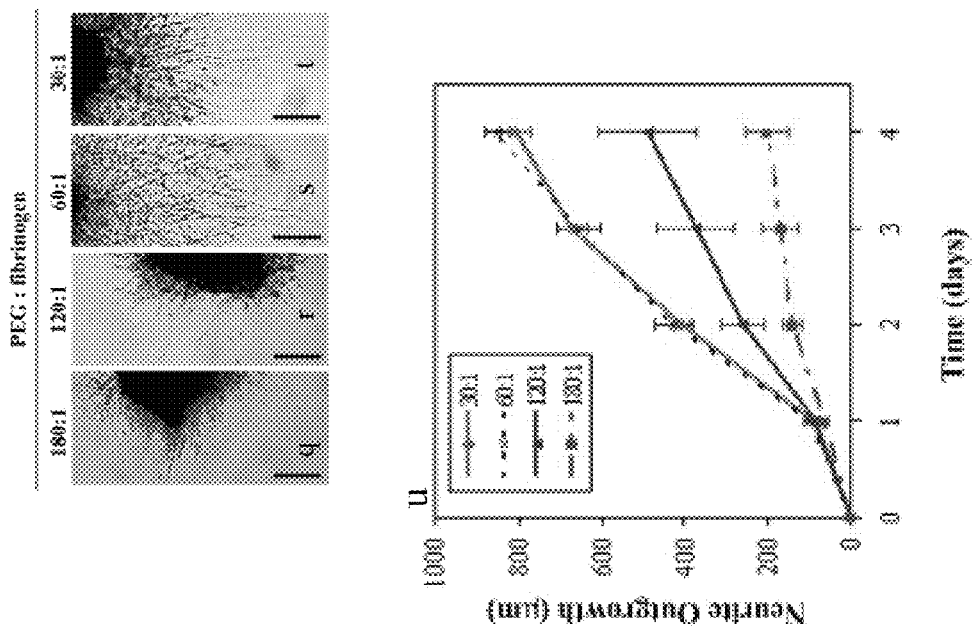
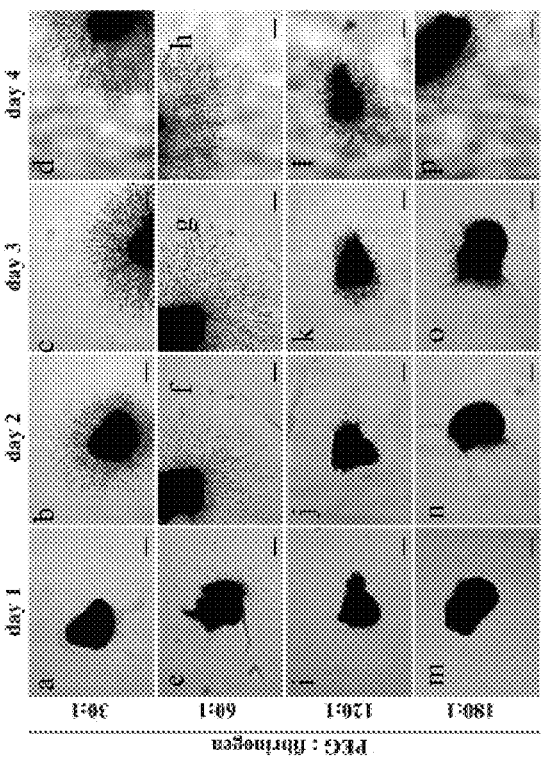

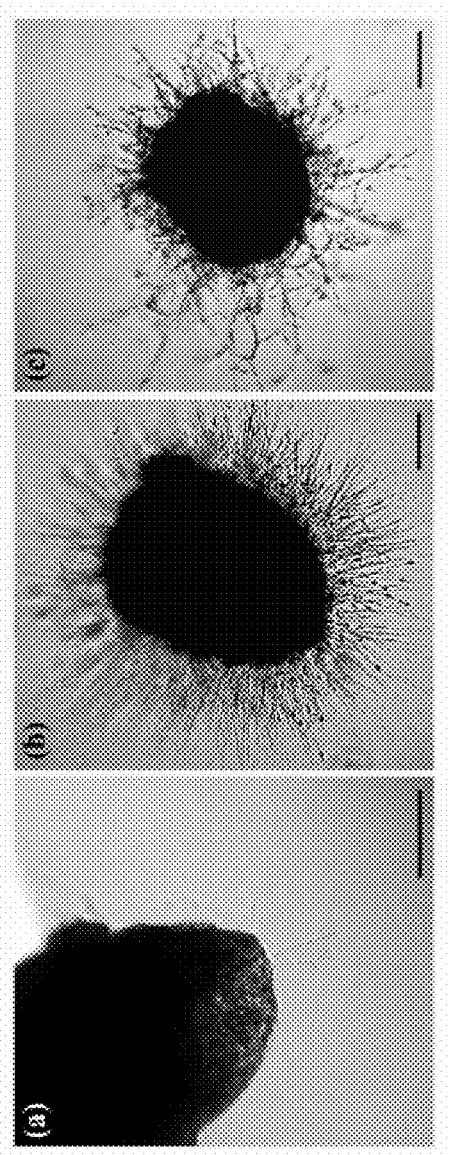
FIGs. 26a-c

```
                          SEQUENCE LISTING

<160> NUMBER OF SEQ ID NOS: 8

<210> SEQ ID NO 1
<211> LENGTH: 3
<212> TYPE: PRT
<213> ORGANISM: Artificial sequence
<220> FEATURE:
<223> OTHER INFORMATION: Fibrinogen derived fragment

<400> SEQUENCE: 1

Arg Gly Asp
1

<210> SEQ ID NO 2
<211> LENGTH: 10
<212> TYPE: PRT
<213> ORGANISM: Artificial sequence
<220> FEATURE:
<223> OTHER INFORMATION: Fibrinogen derived fragment

<400> SEQUENCE: 2

Lys Thr Arg Trp Tyr Ser Met Lys Lys Thr
1               5                   10

<210> SEQ ID NO 3
<211> LENGTH: 20
<212> TYPE: PRT
<213> ORGANISM: Artificial sequence
<220> FEATURE:
<223> OTHER INFORMATION: Fibrinogen derived fragment

<400> SEQUENCE: 3

Lys Thr Arg Trp Tyr Ser Met Lys Lys Thr Thr Met Lys Ile Ile Pro
1               5                   10                  15

Phe Asn Arg Leu
            20

<210> SEQ ID NO 4
<211> LENGTH: 9
<212> TYPE: PRT
<213> ORGANISM: Artificial sequence
<220> FEATURE:
<223> OTHER INFORMATION: Fibrinogen derived fragment
<220> FEATURE:
<221> NAME/KEY: misc_feature
<222> LOCATION: (3)..(4)
<223> OTHER INFORMATION: Xaa can be any naturally occurring amino acid

<400> SEQUENCE: 4

Lys Gly Xaa Xaa Tyr Ser Met Arg Lys
1               5

<210> SEQ ID NO 5
```

```
<211> LENGTH: 6
<212> TYPE: PRT
<213> ORGANISM: Artificial sequence
<220> FEATURE:
<223> OTHER INFORMATION: Fibrinogen derived fragment

<400> SEQUENCE: 5

Leu Phe Glu Tyr Gln Lys
1               5

<210> SEQ ID NO 6
<211> LENGTH: 6
<212> TYPE: PRT
<213> ORGANISM: Artificial sequence
<220> FEATURE:
<223> OTHER INFORMATION: Fibrinogen derived fragment

<400> SEQUENCE: 6

Tyr Met Tyr Leu Leu Lys
1               5

<210> SEQ ID NO 7
<211> LENGTH: 6
<212> TYPE: PRT
<213> ORGANISM: Artificial sequence
<220> FEATURE:
<223> OTHER INFORMATION: Fibrinogen derived fragment

<400> SEQUENCE: 7

Val Lys Glu Leu Ile Lys
1               5

<210> SEQ ID NO 8
<211> LENGTH: 6
<212> TYPE: PRT
<213> ORGANISM: Artificial sequence
<220> FEATURE:
<223> OTHER INFORMATION: Fibrinogen derived fragment

<400> SEQUENCE: 8

His Gln Val Glu Asn Lys
1               5
```

MATRIX COMPOSED OF A NATURALLY-OCCURRING PROTEIN BACKBONE CROSS LINKED BY A SYNTHETIC POLYMER AND METHODS OF GENERATING AND USING SAME

RELATED APPLICATIONS

This application is a Divisional of U.S. patent application Ser. No. 11/472,520 filed on Jun. 22, 2006, which is a continuation-in-part of PCT Patent Application No. PCT/IL2004/001136 filed on Dec. 15, 2004, which claims the benefit of U.S. Provisional Patent Application No. 60/530,917 filed Dec. 22, 2003. The contents of the above applications are all incorporated by reference.

FIELD AND BACKGROUND OF THE INVENTION

The present invention relates to compositions and methods for treating disorders associated with tissue damage, loss, or malformation.

Tissue engineering, i.e., the generation of new living tissues in vitro, is widely used to replace diseased, traumatized or other unhealthy tissues. The classic tissue engineering approach utilizes living cells and a basic scaffold for cell culture (Langer and Vacanti, 1993; Nerem and Seliktar, 2001). Thus, the scaffold structure attempts to mimic the natural structure of the tissue it is replacing and to provide a temporary functional support for the cells (Griffith L G, 2002).

Tissue engineering scaffolds are fabricated from either biological materials or synthetic polymers. Synthetic polymers such as polyethylene glycol (PEG), Hydroxyapatite/polycaprolactone (HA/PLC), polyglycolic acid (PGA), Poly-L-lactic acid (PLLA), Polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and nonbiodegradable polytetrafluoroethylene (PTFE) provide precise control over the physical properties of the material (Drury and Mooney, 2003).

Common scaffold fabrication methods are based on foams of synthetic polymers. However, cell migration into the depth of synthetic scaffolds is limited by the lack of oxygen and nutrient supply. To overcome such limitations, new approaches utilizing solid freeform fabrications and internal vascular architecture have been developed (Reviewed in Sachlos E and Czernuszka J T, 2003; Eur. Cell Mater. 5: 29-39). Likewise, freeze-drying methods are also employed to create unique three-dimensional architectures with distinct porosity and permeability. However, creating pores into these materials is an aggressive procedure, often involving the use of toxic conditions which eliminate the possibility of pre-casting tissue constructs with living cells. Therefore, many of the prefabricated materials are subject to uneven cell seeding and inhomogeneous populations of cells within the constructs. Furthermore, the materials are generally degraded unevenly during the tissue cultivation process, creating a highly anisotropic tissue with altered growth kinetics.

Scaffolds made of PEG are highly biocompatible (Merrill and Salzman, 1983) and exhibit versatile physical characteristics based on their weight percent, molecular chain length, and cross-linking density (Temenoff J S et al., 2002). In addition, PEG hydrogels are capable of a controlled liquid-to-solid transition (gelation) in the presence of cell suspension (Elbert and Hubbell, 2001). Moreover, the PEG gelation (i.e., PEGylation) reaction can be carried out under non-toxic conditions in the presence of a photoinitiator (Elisseeff J et al., 2000; Nguyen and West, 2002) or by mixing a two-part reactive solution of functionalized PEG and cross-linking constituents (Lutolf and Hubbell, 2003).

However, while the abovementioned synthetic polymers enable precise control over the scaffold material, they often provide inadequate biological information for cell culture. As a result, these materials are unsuitable for long-term tissue culture or in vivo tissue regeneration.

On the other hand, naturally occurring scaffolds such as collagen, fibrin, alginate, hyaluronic acid, gelatin, and bacterial cellulose (BC) provide bio-functional signals and exhibit various cellular interactions. For example, fibrin, a natural substrate of tissue remodeling (Herrick S., et al., 1999), contains several cell-signaling domains such as a protease degradation substrate (Werb Z, 1999) and cell-adhesion domains (Herrick S., 1999). However, because such biological materials exhibit multiple inherent signals (e.g., regulation of cell adhesion, proliferation, cellular phenotype, matrix production and enzyme activity), their use as scaffolds in tissue regeneration often results in abnormal regulation of cellular events (Hubbell, 2003). Furthermore, the natural scaffolds are often much weaker after reconstitution as compared to the strength of the original biological material, and little control can be exercised to improve their physical properties.

Another drawback of natural scaffolds (e.g., collagen and fibrin) for tissue engineering is the limited control over the physical properties of the polymeric network. For example, reconstituted collagen undergoes fibrilogenesis and self-assembly to form an interpenetrating network of nano-scale fibrils that loosely associate together by non-specific interactions such as hydrogen bonding. In comparison to the highly organized and enzymatically cross-linked collagen fibers of the normal tissue structure, the interpenetrating network of fibrils exhibit poor physical strength and super-physiological tissue porosity. Moreover, the specific conformation of fibrils combined with the open pore structure of the interpenetrating network leaves the protein backbone easily accessibly and susceptible to freely diffusing proteases from the surrounding host tissue or cell culture system. This often results in uncontrolled and premature deterioration of the scaffold in the presence of cell-secreted proteases. The discrepancies in structure and function of reconstituted protein hydrogels compared to natural urges the development of biomimetic scaffold systems for implementation in many practical tissue engineering applications.

To date a number of techniques have been developed for the modification and improvement of the physicochemical properties of reconstituted protein hydrogels which prevent them from rapid degradation. Collagen and fibrin hydrogels can be processed by freeze-drying the construct to increase the tensile strength and modulus of the protein network. However, freeze-drying necessitates a pre-fabrication freezing step which eliminates the possibility for gelation of the polymer in the presence of cells and also eliminates the benefits of in-situ polymerization. The freeze-drying process also affects the molecular architecture of the polymer network, altering the nano-fiber mesh and turning it into a macro-porous sponge structure. Other techniques for improving the physical properties of natural hydrogels while maintaining the nano-fiber structure have been proposed based on covalent cross-links, including the use of aldehydes, carbodiimides [Park S N, Park J C, Kim H O, Song M J, Suh H. Characterization of porous collagen/hyaluronic acid scaffold modified by 1-ethyl-3-(3-dimethylaminopropyl)carbodiimide cross-linking. Biomaterials. 2002 February; 23(4):1205-12], and N-hydroxysuccinimides (NHS) in the presence of amino acids [Ma L, Gao C, Mao Z, Zhou J, Shen J. Enhanced biological stability of collagen porous scaffolds by using amino acids as novel cross-linking bridges. Biomaterials. 2004 July; 25(15):2997-3004; Ma L, Gao C, Mao Z, Zhou J, Shen J. Biodegradability and cell-mediated contraction of porous collagen scaffolds: the effect of lysine as a novel crosslinking bridge. J Biomed Mater Res A. 2004 Nov. 1; 71(2):334-42]. All the cross-linking procedures offer some improvements of the physical stability of the scaffold, but do so by introducing a toxic manufacturing step which requires extensive washes and increases the likelihood that residual toxins in the scaffold will affect cellular activity.

The proteolytic degradation of protein scaffolds can also be delayed by protecting the protein backbone of the polymer network using covalent attachment of a shielding polymers such as poly(ethylene glycol) (PEG). For example, the modification of proteins by attachment of one or more PEG chains (PEGylation) has been applied very successfully to increasing the plasma half-life of therapeutic peptides or protein drugs [Veronese F M. Peptide and protein PEGylation: a review of problems and solutions. Biomaterials. 2001 March; 22(5):405-17]. Based on a similar rationale, PEGylation could be a good strategy for protein-based biomaterial design in as much as the PEG chains can slow down the enzymatic biodegradation of the PEGylated protein scaffold. At the same time, the PEG chains are non-toxic, non-immunogenic, highly water soluble, and are already approved by the FDA in a number of different clinical indications (Veronese, 2005). Common proteins used in scaffold design such as collagen and fibrin may be readily PEGylated using amine group modifications or thiol modifications of the protein backbone to yield a protein-polymer conjugate. The PEG shields the protein surface from degrading agents by steric hindrances without blocking all the natural biological function of the structural protein molecule (Veronese 2005).

Recently hybrid scaffolds have been developed. A hybrid scaffold material combines the structural characteristics of the synthetic material with the biofunctionality of natural material (Leach J B, et al., 2004; Leach and Schmidt, 2005). To this end, several methods of preparing scaffold with natural biofunctionality and physical properties of synthetic polymers have been proposed. Most of these "hybrid" approaches, however, fall short of producing a biomaterial with broad inherent biofunctionality and a wide range of physical properties; mainly because they employ only a single biofunctional element into the material design. For example, prior studies describe the preparation of scaffolds consisting of biodegradable elements grafted into the backbone of a synthetic hydrogel network. Hydrogels were prepared from synthetic PEG which was cross-linked with short oligopeptides containing enzymatic substrates capable of being proteolytically degraded by cell-secreted enzymes [Lutolf et al (2003); Gobin and West (2002)]. Furthermore, to increase the biofunctionality of such hydrogels, synthetic adhesion motifs such as the RGD sequences [Lutolf et al (2003)] or VEGF (Seliktar et al; 2004, Zisch A H, et al, 2003; FASEB J. 17: 2260-2. Epub 2003 Oct. 16) were grafted into the PEG backbone. However, the use of such scaffolds (in which PEG is the major component) was limited by the insufficient bio-feedback and/or long-term cellular responses which are essential for phenotypic stability.

Further attempts to increase the biofunctionality of the scaffolds included the manufacture of genetically-engineered protein-like precursors of 100 amino acids, which contain, among other things, several protease substrates and adhesion sites (Halstenberg et al. 2002; Biomacromolecules, 3: 710-23). However, the increased protein precursors size and the presence of thiol groups required for the PEGylation reaction complicated the purification and solubilization of the precursors during the scaffold manufacturing process. In addition, similar to the PEG-based biosynthetic materials, the genetically-engineered protein precursor scaffolds failed to provide sufficient biofunctionality to enable long-term stability.

The present inventor has previously uncovered that biosynthetic hybrid scaffolds composed of a fibrinogen backbone which is cross-linked with functional polyethylene glycol (PEG) side chains are excellent, biodegradable scaffolds which can be used for tissue regeneration applications.

While reducing the present invention to practice, the present inventor has uncovered that the above scaffold are subject to the proteolytic and hydrolytic activity of the cellular environment in the implantation site causing sustained release of PEGylated denatured fibrinogen degradation products. These PEGylated denatured fibrinogen degradation products have similar inductive properties of the natural fibrin degradation products with the added advantage of the PEG modification which provides protection from rapid clearance from the local implantation site and from the body.

SUMMARY OF THE INVENTION

According to one aspect of the present invention there is provided a composition-of-matter comprising a synthetic polymer attached to denatured fibrinogen or a therapeutic portion of said denatured fibrinogen.

According to another aspect of the present invention there is provided a scaffold comprising the composition-of-matter.

According to yet another aspect of the present invention there is provided a hydrogel comprising the composition-of-matter.

According to further features in preferred embodiments of the invention described below, said denatured fibrinogen is fragmented denatured fibrinogen and whereas a concentration of said units in said hydrogel is selected from a range of 0.5-35%.

According to still further features in the described preferred embodiments, modulus of elasticity of said hydrogel is in a range of 0.02-0.11 kPa for 10-20% polymer.

According to still further features in the described preferred embodiments modulus of elasticity of said hydrogel is in a range of 0.01-0.07 kPa for 10-20% polymer.

According to still another aspect of the present invention there is provided a medical device comprising the composition-of-matter.

According to still further features in the described preferred embodiments the medical device is an intracorporeal device.

According to still further features in the described preferred embodiments the medical device is an extracorporeal device.

According to still further features in the described preferred embodiments the medical device is selected from the group consisting of a prosthetic device, a pacemaker, an artificial joint, a heart valve replacement, temporary implant, a permanent implant, a stent, a vascular graft, an anastomotic device, a clamp, an aneurysm repair device and an embolic device.

According to an additional aspect of the present invention there is provided a pharmaceutical composition comprising the composition-of-matter.

According to another aspect of the present invention there is provided a method of treating a disorder characterized by a tissue damage, the method comprising providing to a subject in need-thereof a composition which comprises a synthetic polymer attached to denatured fibrinogen or a therapeutic portion of said fibrinogen, said composition being formulated for releasing said therapeutic portion of said fibrinogen in a pharmacokinetically regulated manner, thereby treating the disorder characterized by tissue damage or malformation.

According to still further features in the described preferred embodiments the composition-of-matter further comprising a pharmaceutical agent.

According to still further features in the described preferred embodiments said pharmacokinetically regulated manner is immediate releasing of said therapeutic portion of said fibrinogen.

According to still further features in the described preferred embodiments said pharmacokinetically regulated manner is sustained releasing of said therapeutic portion of said fibrinogen.

According to still further features in the described preferred embodiments said sustained releasing of said therapeutic portion of said fibrinogen is between 1 week and 200 weeks.

According to still further features in the described preferred embodiments said composition is comprised in a scaffold, medical device, pharmaceutical composition or a hydrogel.

According to still further features in the described preferred embodiments said composition is formulated for local administration.

According to still further features in the described preferred embodiments said composition is formulated for systemic administration.

According to still further features in the described preferred embodiments said therapeutic portion of said denatured fibrinogen is an enzyme cleavage product of said denatured fibrinogen.

According to still further features in the described preferred embodiments said enzyme is selected from the group consisting of plasmin, collagenase and trypsin.

According to still further features in the described preferred embodiments said therapeutic portion of said denatured fibrinogen is synthetic.

According to still further features in the described preferred embodiments said therapeutic portion of said denatured fibrinogen is as set forth in SEQ ID NO: 1, 2, 3, 4, 5, 6, 7 or 8.

According to still further features in the described preferred embodiments said synthetic polymer is selected from the group consisting of polyethylene glycol (PEG), Hydroxyapatite/polycaprolactone (HA/PLC), polyglycolic acid (PGA), Poly-L-lactic acid (PLLA), Polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and nonbiodegradable polytetrafluoroethylene (PTFE).

According to still further features in the described preferred embodiments said PEG is selected from the group consisting of PEG-acrylate (PEG-Ac) and PEG-vinylsulfone (PEG-VS).

According to still further features in the described preferred embodiments said PEG-Ac is selected from the group consisting of PEG-DA, 4-arm star PEG multi-Acrylate and 8-arm star PEG multi-Acrylate.

According to still further features in the described preferred embodiments said PEG-DA is a 4-kDa PEG-DA, 6-kDa PEG-DA, 10-kDa PEG-DA and/or 20-kDa PEG-DA.

According to still further features in the described preferred embodiments a molar ratio between said PEG-DA to said denatured fibrinogen or said therapeutic portion is 2-400 to 1.

According to still further features in the described preferred embodiments a molar ratio between said PEG-DA to said fibrinogen or said therapeutic portion is 25 to 1.

According to still further features in the described preferred embodiments a molar ratio between said PEG-DA to said fibrinogen or said therapeutic portion is 75 to 1.

According to still further features in the described preferred embodiments a molar ratio between said PEG-DA to said fibrinogen or said therapeutic portion is 150 to 1.

According to yet an additional aspect of the present invention there is provided an article-of-manufacturing comprising a packaging material and the composition identified for treating a disorder characterized by a tissue damage or malformation.

The present invention successfully addresses the shortcomings of the presently known configurations by providing compositions and methods for inducing tissue regeneration.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. The file of this patent contains at least one drawing executed in color photograph. Copies of this patent with color photograph(s) will be provided by the Patent and Trademark Office upon request and payment of necessary fee.

In the drawings:

FIGS. 5a-d depict the in vitro degradation kinetics of denatured PEGylated fibrinogen precursor (whole) into degradation products by trypsin (FIGS. 5a-b) and collagenase (FIGS. 5c-d).

FIGS. 6a-j are photographs depicting smooth muscle cells migration from smooth muscle tissue into PEG-Fibrinogen containing hydrogel matrix. Smooth muscle tissue constructs were encapsulated by PEG-fibrinogen hydrogel and visualized by phase-contrast microscopy. Cellular invasion from the dense tissue (opaque) into the hydrogels (transparent) was seen within several hours following hydrogel casting and throughout the experiment (FIGS. 6a-c). Macroscopically, the tissue construct (arrow) was entrapped within the PEG-fibrinogen hydrogel (FIGS. 6d-e). Of note, the hydrogel maintained its structural stability even following one week in culture (FIG. 6f). The degradation kinetics and invasion kinetics were affected by the amount relative composition of PEG-DA and denatured fibrinogen in hydrogel; the cells became more polarized and oriented radially outward from the tissue construct as they invaded PEG-fibrinogen matrix containing higher concentrations of 10-kDa PEG-DA (FIG. 6g—0%; FIG. 6h—0.5%; FIG. 6i—1.0%; FIG. 6j—2.0%). Phase contrast micrographs were imaged at 40× magnification (scale bar=250 μm);

FIGS. 7a-d are illustrate cellular invasion resultant of the chemotactic activity of degrading denatured PEGylated fibrinogen hydrogels. FIG. 7a shows the invasion kinetics data during one-week culture of smooth muscle cells invading into 10-kDa PEGylated fibrinogen hydrogels made with additional PEG-DA. FIG. 7b shows the summary of invasion data for 6-kDa and 10-kDa PEGylated fibrinogen hydrogels during one week. FIG. 7c-d depict stem cell and cartilage cell invasion into hydrogel materials releasing denatured PEGylated fibrinogen degradation products. Each image shows an in vitro culture of a three-dimensionally entrapped living, natural tissue explants within a dense hydrogel matrix. FIG. 7c shows human embryoid bodies (EB) cultured for 8 days demonstrating embryonic stem cell sprouting from the EB into the dense gel matrix. FIG. 7d shows cartilage explants (CE) cultured for 14 days exhibiting massive cell invasion from the native tissue into the encapsulating gel matrix.

FIGS. 8a-d are photographs depicting the generation of a site-specific defect in the rat's tibia. FIG. 8a—The mid-portion of the right tibia was exposed from the anterior medial side by longitudinal incision; FIG. 8b—An external fixation device was placed proximal and distal to the mid-section of the tibia; FIG. 8c—A 7-mm gap was excised in the portion between the proximal and distal needles of the fixation device; and FIG. 8d—A PEG-fibrinogen containing plug was inserted into the defect site.

FIGS. 10a-b are photomicrographs depicting newly formed subperiosteal and endosteoal bone shown with partially degraded hydrogel in a longitudinal section of an intermediate-degrading treatment. FIG. 10a—The osseous trabeculae, which connect with one another, are rimmed by active cuboidal osteoblasts. The intertrabecular spaces are occupied by a fatty marrow (FM), which well extends into the site of the defect from the aspect of the medial osteotomy (ost). A cartilaginous cap (arrows) at the medial end of the front of regenerated bone is seen with islets of hypertrophic chondrocytes. The cap is enclosed by a thin layer of perichondrium-like fibrous tissue. Fibro-fatty tissue (FT) is present in between the degraded hydrogel and the regenerated bone. FIG. 10b—This field (taken at higher magnification) displays endochondrol ossification (ECO) in the cartilaginous region. The sections are stained with hematoxylin and eosin (H&E);

FIGS. 11a-b are photomicrographs depicting cellular response to the PEG-fibrinogen containing hydrogel implant. FIG. 11a shows a serpentine granulation tissue at the eroding front of the hydrogel (solid arrows) with an adjacent nonspecific chronic inflammatory infiltrate, which is primarily composed of lymphocytes (LR) and is accompanied by newly formed bone (NB). In certain areas of the tissue-material interface, the response is limited to a minor chronic nonspecific inflammatory reaction (dashed arrow). The eosinophilic hydrogel is lightly stained and shows no cellular infiltration beyond the eroding borders of the dense matrix (gel). FIG. 11b is a high magnification micrograph showing the pallisading granulation tissue. Of note is the minor macrophagic reaction (MR).

FIGS. 12a-d are pictures showing implantation of denatured fibrinogen implant in oseteochondral defects. FIG. 12a shows gross appearance of four osteochondral defects, 6-mm in diameter situated in the femoral condyle in the right-stifle joint. FIG. 12b shows the PEGylated denatured fibrinogen implant polymerized in situ in the osteochondral defect. FIGS. 12c-d show an operating room scene where the surgeon injects the polymer solution into the defect site and polymerizes the solution in situ using a UV light source and a fiber-optic light guide.

FIGS. 13a-d are pictures showing the gross appearance of osteochondrol defects on the day of operation (FIGS. 13a-b) and 4 months, following, during tissue harvest. A newly formed articular (hyaline) cartilage surface is seen in treated defects (1, 2, 5) whereas the empty control defect appears dramatically different. FIG. 13a-patellar notch day of operation; FIG. 13b-femoral condyle day of operation; FIG. 13c-patellar notch 4 months post-operative; FIG. 13d-femoral condyle 4 months post-operative.

FIGS. 14a-d are longitudinal histological sections of the 6-mm osteochondral defects 4 months following implantation. The defects are either left empty (FIG. 14a empty control) or treated with hydrogels of denatured PEGylated fibrinogen (FIGS. 14b-d) with different concentrations of PEG and fibrinogen in each treatment. Histology is shown for treatments with (FIG. 14b) 150:1 molar ratio of PEG to fibrinogen, (FIG. 14c) 200:1 molar ratio of PEG to fibrinogen, and (FIG. 14d) 350:1 molar ratio PEG to fibrinogen in the defect site. All treated defects showed impressive regeneration of both cartilage and bone surrounding the eroding PEGylated fibrinogen implant. In all the histological sections of the treated defects, the acellular gel is seen and marked in the middle of the H&E stained section.

FIG. 18a shows a thin layer of an inflammatory infiltrate surrounding the eroding implant. A higher magnification image of this interface (FIG. 18b) shows the implant, the inflammatory response and the newly formed cartilage and bone cells.

FIGS. 19a-d are high magnification images of articular cartilage repair showing the newly formed hyaline cartilage in the PEGylated fibrinogen treated defects with (FIGS. 19a-b) 150:1 molar ratio PEG to fibrinogen and (FIGS. 19c-d) 350:1 molar ratio PEG to fibrinogen.

FIGS. 20a-f show the integration of the defect site with the newly formed hyaline cartilage in the sheep osteochondral defect model. FIG. 20a shows the original dimensions of the defect site which is marked by short arrows. FIGS. 20c-f show longitudinal high magnification images of the entire length of the newly formed articular cartilage highlight the extent and quality of healing. Integration between the new and old cartilage is marked by long arrows in (FIG. 20b) and (FIG. 20f).

FIGS. 21a-c are photographs showing the encapsulation of a single dorsal root ganglion (DRG) into a PEGylated fibrinogen hydrogel. FIG. 21a illustrates that the DRG (arrow) is roughly 0.5 mm in diameter and is situated in the center of a 10 mm diameter PEGylated fibrinogen hydrogel. Radial outgrowth is measured from the outer boundary of the opaque DRG into the transparent hydrogel. The same constructs is shown from the top view (FIG. 21b) and the side view (FIG. 21c).

FIGS. 22a-d are photomicrographs showing outgrowth and cellular invasion characteristics of DRGs in PEGylated fibrinogen 3-D hydrogel constructs. Phase-contrast micrographs (FIGS. 22a and 22b) show the three-dimensional outgrowth of neurites (arrow) and glial cells (arrowhead) extending from the DRG (D) into the transparent PEGylated fibrinogen hydrogel construct (P) following two days in culture. Histological sections stained with H&E (FIGS. 22c and 22d) of the DRG (dark) in the PEGylated fibrinogen construct (light) show neurite (arrow) and non-neuronal cells (arrowhead) invading the hydrogels after four days in culture. Note: high magnification images (FIGS. 22b and 22d) are expanded regions from the lower magnification micrographs (FIGS. 22a and 22c); in all images the scale bar=100 µm.

FIGS. 23a-f are fluorescent microscope images of DRGs encapsulated in PEGylated fibrinogen constructs confirming the presence of both neurites and schwann cells. Cross sections of DRG constructs were cultured for four days and fluorescently triple-labeled with βIII-tubulin (neurite marker, FIGS. 23a and 23d), s100 (Schwann cell marker, FIGS. 23b and 23e), and DAPI counter-stain (nuclei, blue). The merged micrographs (FIGS. 23c and 23f) show the three-dimensional invasion of neurites from the DRG into the hydrogel construct, with Schwann cells associated very closely with the neurite extensions (scale bar=50 µm).

FIGS. 24a-d are fluorescent microscope images and graphs showing that both free soluble and enmeshed nerve growth factor (FS-NGF and EN-NGF) promote 3-D neurite outgrowth from encapsulated DRGs into the hydrogels. Sections of DRG constructs following four days were immunofluorescently labeled for βIII-tubulin (neurites, red), s100 (Schwann cells, green) and DAPI nuclear stain (blue) to characterize the invasion into the hydrogels containing FS-NGF (FIG. 24a), EN-NGF (FIG. 24b), or no NGF (NO-NGF; FIG. 24c). Absence of NGF (NO-NGF) did not encourage outgrowth of neurites but supported moderate outgrowth of Schwann cells. Treatments with free soluble or enmeshed NGF exhibited impressive outgrowth of both neurites and Schwann cells (scale bar=50 µm). FIG. 24d is a line graph illustrating that the average neurite extension length (±standard error) in free soluble NGF treatments (FS-NGF) and enmeshed NGF treatments (EN-NGF) is not significantly different between the two treatments (P>0.35, n=6).

FIGS. 25a-u are phase contrast micrographs and graphs showing that PEG-fibrinogen composition controls neurite invasion and outgrowth. The hydrogel composition is varied using different amounts of PEG and fibrinogen during assembly, including 30:1, 60:1, 120:1, and 180:1 (PEG:Fibrinogen). FIGS. 25a-p are phase contrast micrographs showing the profound impact of additional PEG on the 3-D outgrowth morphology from the DRG following four days (scale bar=200 µm). FIGS. 25q-t are high magnification images showing the relative outgrowth of neurites and glial cells into hydrogels having different compositions (scale bar=200 µm). FIG. 25u is a line graph showing that the average neurite extension length (±standard error) in each treatment, as measured directly from the images, shows no significant difference between the 30:1 and 60:1 treatments (P>0.50, n=9), and a significant impediment to outgrowth in the 120:1 and 180:1 treatments (p<0.01, n=9).

FIGS. 26a-c are phase contrast micrographs showing DRG outgrowth into hydrogels made from PEG-DA and PEG-fibrinogen. Constructs were prepared with 10% PEG-DA gels (w/v) without fibrinogen (FIG. 26a) and compared with PEG-fibrinogen constructs (FIG. 26b). Neurite extensions were barely visible following three days in PEG-DA construct compared to extensive invasion seen in PEGylated fibrinogen constructs after three days. Neuronal invasion into PEGylated fibrinogen hydrogels was eliminated in the absence of NGF (FIG. 26c), although other cells types were observed in the hydrogel following three days in culture. In all images the scale bar=200 μm.

DESCRIPTION OF THE PREFERRED EMBODIMENTS

Figure 1A:
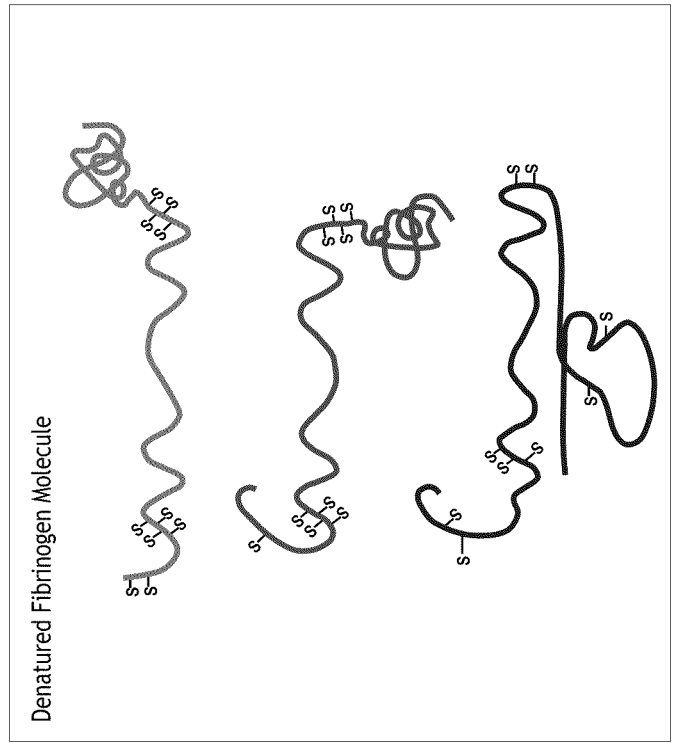
FIGS. 1*a-b* is a scheme depicting denaturation of purified fibrinogen molecules. The heteromeric fibrinogen is comprised of two subunits of three chains each, held together by disulfide rings. Reducing the disulfide bonds and denaturation of the fibrinogen in Urea and beta-mercaptoethanol results in 2 sets of 3 chains of denatured protein (3 chains are shown).

The present invention is of novel compositions which can be used for treating tissue damage, loss or malformation.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Material technologies have long been harnessed for tissue regeneration applications. Biomaterials used in tissue regeneration are composed of natural or biological materials, synthetic materials, and biosynthetic composite or hybrid materials. Natural materials such as collagen and fibrinogen, may exert uncontrolled cell signaling and may introduce uncertainty in the regulated communication between the biomaterial and cells. Moreover, the inherent structural characteristics of biological materials are not easily altered, thus limiting control over physical cues received by the surrounding cells and tissues. Synthetic scaffolds are generated mostly from biologically inactive (inert) materials that are easily manipulated, rendering these ideal for regulating the physical interactions between cells and biomaterial at the biomaterial-tissue interface. However, synthetic scaffolds may inadvertently participate in random biological signaling caused by absorption of serum proteins, for example, and subsequent activation of cells through contact with these proteins. Biosynthetic composite materials are a complementary blend of natural and synthetic materials designed to regulate between the physical and biological cell signaling of the scaffold.

The present inventor has previously uncovered that biosynthetic hybrid scaffolds composed of a fibrinogen backbone which is cross-linked with functional polyethylene glycol (PEG) side chains are excellent, biodegradable scaffolds which can be used for tissue regeneration applications (see WO2005/055800).

While reducing the present invention to practice, the present inventor has uncovered that once implanted the above scaffolds are subject to the proteolytic and hydrolytic activity of the cellular environment causing sustained release of PEGylated denatured fibrinogen degradation products. These PEGylated denatured fibrinogen degradation products have similar inductive properties of the natural fibrin degradation products with the added advantage of the PEG modification (PEGylation) and which provides protection from rapid clearance from the local implantation site and from the body. Such compositions may be formulated for releasing therapeutically active fibrin fragments in a pharmacokinetically regulated manner, allowing the treatment of a myriad of diseases associated with tissue damage, loss or malformation.

Thus, as is illustrated hereinbelow and in the Examples section which follows, the present inventor designed a biosynthetic hybrid fibrinogen precursor by subjecting cleaved or whole denatured fibrinogen to PEGylation, possibly generating a three dimensional (3D) matrix therefrom (see Example 1). The present inventor further showed that degradation products released from the above scaffold have a chemotactic activity as shown in an in vitro tissue culture assay (see Example 3). The fibrinogen precursors were formulated of various PEG:denatured fibrinogen ratios for controlling release of the active products at the site of implantation. Such formulations were shown effective in bone and cartilage regeneration in animal models of injury (see Examples 4 and 5).

Thus, according to the present invention there is provided a method of treating a disorder characterized by tissue damage. The method comprising providing to a subject-in-need-thereof a therapeutically effective amount of a composition which comprises a synthetic polymer attached to fibrinogen or a therapeutic portion of the fibrinogen, the composition being formulated for releasing the therapeutic portion of the fibrinogen in a pharmacokinetically regulated manner, thereby treating the subject having the disorder characterized by tissue damage.

As used herein the term "subject" refers to an animal subject, such as a mammal, preferably a human subject.

As used herein the term "treating" refers to alleviating or diminishing a symptom associated with a disorder. Preferably, treating cures, e.g., substantially eliminates, the symptoms associated with the disorder.

As used herein the phrase "disorder characterized by a tissue damage" refers to a disorder, disease or condition which is caused by or associated with a non functioning tissue (i.e., cancerous or pre-cancerous tissue, wounded tissue, broken tissue, fractured tissue, fibrotic tissue, or ischemic tissue); and/or tissue loss (reduced amount of functioning tissue) such as following a trauma, an injury or abnormal development (i.e., malformation, —structural defect that occurs infrequently such as due to abnormal development which require tissue regeneration). Preferably the tissue is a functional tissue such as a bone tissue, a cartilage tissue, a tendon tissue, ligament, a cardiac tissue, a nerve tissue, or a muscle tissue.

Examples of disorders characterized by a tissue damage include, but are not limited to, cartilage damage (articular, mandibular), bone cancer, osteoporosis, bone fracture or deficiency, primary or secondary hyperparathyroidism, osteoarthritis, periodontal disease or defect, an osteolytic bone disease, post-plastic surgery, post-orthopedic implantation, post-dental implantation, cardiac ischemia, muscle atrophy, and nerve degeneration.

As mentioned in the above subject is administered with a composition which comprises a synthetic polymer attached to the denatured fibrinogen or a therapeutic portion of the denatured fibrinogen.

As used herein "denatured fibrinogen" refers to each of the 6 chains composing fibrinogen which is formed by any mode of specific (disulfide) and non-specific (hydrogen bond) denaturation such as by thermal denaturation, freeze-drying, alkali denaturation and chelator (e.g., EGTA) mediated denaturation [Haddeland (1995) Thromb. Res. 77:329-36]. Denatured fibrinogen may comprise a whole fibrinogen chain or a therapeutic portion thereof.

As used herein "a therapeutic portion of fibrinogen" refers to a fibrinogen portion which is sufficient to mediate a fibrinogen activity, such as cell proliferation, angiogenesis or anti-inflammatory activity.

The amino acid length of the therapeutic portion of fibrinogen may vary. Such as at least 3 amino acids long (e.g., 3-20, 3-50, 3-100, 3-200, 3-300, 3-400, 3-500 amino acids).

Examples of therapeutic portions of fibrinogen are provided in SEQ ID NOs. 1-8 (see e.g., U.S. Pat. Nos. 5,427,918, 5,473,051, 5,919,754; U.S. Pat. Appl. Nos. 20030109431, 20050020809, 20040126758, 20040029157).

Therapeutic portions of fibrinogen may be generated by enzymatic cleavage of fibrinogen using one or more enzymes which cleave fibrinogen. Examples of such enzymes include, but are not limited to, plasmin, collagenase and trypsin. See example 2 of the Examples section which follows.

Alternatively, therapeutic portions of the denatured fibrinogen may be generated by a proteolytic chemical such as cyanogen bromide and 2-nitro-5-thiocyanobenzoate.

Yet alternatively, therapeutic portions of denatured fibrinogen may be generated using synthetic or recombinant techniques which are well known in the art.

Synthetic peptides can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield, J. Am. Chem. Soc., 85:2149 (1963), incorporated herein by reference. Solid phase peptide synthesis procedures are well known in the art and further described by John Morrow Stewart and Janis Dillaha Young, Solid Phase Peptide Syntheses (2nd Ed., Pierce Chemical Company, 1984).

Regardless of the method employed, once therapeutic portions are generated they may be used in a batch which comprises a mixture of therapeutic portions with or without inactive portions, or alternatively, isolated and purified (e.g., medical purity e.g., over 95% purity). In this regard, it will be appreciated that while some molecules may not have a therapeutic effect, such molecules can still serve in combination with those having a therapeutic effect, as part of the carrier in a formulation, such as further described herein below. Essaying therapeutic activity of fibrinogen products may be effected using methods which are well known in the art such as cell proliferation or migration assay, described in length in the Examples section which follows.

Thus, therapeutic products can be purified by preparative high performance liquid chromatography [Creighton T. (1983) Proteins, structures and molecular principles. WH Freeman and Co. N.Y.], gel electrophoresis and the composition of which can be confirmed via amino acid sequencing.

As mentioned, denatured fibrinogen or portions thereof are attached (i.e., covalently attached) to a synthetic polymer. Methods of covalently attaching synthetic polymers to fibrinogen are well known in the art and described in Example 1 of the Examples section.

Non-limiting examples for synthetic polymers which can be used along with the present invention include polyethylene glycol (PEG) (average Mw. 200; P3015, SIGMA), Hydroxyapatite/polycaprolactone (HA/PLC) [Choi, D., et al., 2004, Materials Research Bulletin, 39: 417-432; Azevedo M C, et al., 2003, J. Mater Sci. Mater. Med. 14(2): 103-7], polyglycolic acid (PGA) [Nakamura T, et al., 2004, Brain Res. 1027(1-2): 18-29], Poly-L-lactic acid (PLLA) [Ma Z, et al., 2005, Biomaterials. 26(11): 1253-9], Polymethyl methacrylate (PMMA) [average Mw 93,000, Aldrich Cat. No. 370037; Li C, et al., 2004, J. Mater. Sci. Mater. Med. 15(1): 85-9], polyhydroxyalkanoate (PHA) [Zinn M, et al., 2001, Adv. Drug Deliv. Rev. 53(1): 5-21; Sudesh K., 2004, Med. J. Malaysia. 59 Suppl B: 55-6], poly-4-hydroxybutyrate (P4HB) [Dvorin E L et al., 2003, Tissue Eng. 9(3): 487-93], polypropylene fumarate (PPF) [Dean D, et al., 2003, Tissue Eng. 9(3): 495-504; He S, et al., 2000, Biomaterials, 21(23): 2389-94], polyethylene glycol-dimethacrylate (PEG-DMA) [Oral E and Peppas N A J, 2004, Biomed. Mater. Res. 68A(3): 439-47], beta-tricalcium phosphate (beta-TCP) [Dong J, et al., 2002, Biomaterials, 23(23): 4493-502], and nonbiodegradable polytetrafluoroethylene (PTFE) [Jernigan T W, et al., 2004. Ann. Surg. 239(5): 733-8; discussion 738-40].

According to a presently preferred embodiment of the present invention the synthetic polymer used by the present invention is PEG. The PEG molecule used by the present invention can be linearized or branched (i.e., 2-arm, 4-arm, and 8-arm PEG) and can be of any molecular weight, e.g., 4 kDa, 6 kDa and 20 kDa for linearized or 2-arm PEG, 14 kDa and 20 kDa for 4-arm PEG, and 14 kDa and 20 kDa for 8-arm PEG and combination thereof.

According to a presently known preferred embodiment of the present invention, a 6-14 kDa PEG-diacrylate is used.

It will be appreciated that the OH-termini of the PEG molecule can be reacted with a chemical group such as acrylate (Ac) or vinylsulfone (VS) which turn the PEG molecule into a functionalized PEG, i.e., PEG-Ac or PEG-VS. Preferably, the PEG molecule used by the present invention is PEG-Ac. Alternatively; the PEG can be modified with a pyridildisulphide group, a maleimide group, or a iodo acetamide group. Other functional groups include carbonates such as benzotriazolyl carbonate and succinimidyl carbonate [see review by Veronese F and Paust G, Drug Discovery Reviews, vol 10 (21), November 2005].

Methods of preparing functionalized PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-Ac is made under argon by reacting a DCM solution of the PEG-OH with acryloyl chloride and triethylamine (molar ratios: OH 1: acryloyl chloride 1.5: triethylamine 2, at 0.2 gram PEG/mL DCM), essentially as described in Example 1 of the Examples section which follows.

It will be appreciated that such chemical groups can be attached to linearized, 2-arm, 4-arm, or 8-arm PEG molecules.

Preferably, the PEG-Ac used by the present invention is PEG-DA, 4-arm star PEG multi-Acrylate and/or 8-arm star PEG multi-Acrylate.

As is shown in Example 1 of the Examples section which follows the present inventor used various isoforms of PEG-diacrylate (PEG-DA) to prepare functionalized PEG molecules.

As mentioned hereinabove, the above precursor composition (i.e., synthetic polymer attached to denatured fibrinogen or a therapeutic portion of same) is formulated for releasing the therapeutic portion of the fibrinogen in a pharmacokinetically regulated manner. One of ordinary skill in the art will choose the formulation according to the intended use.

The pharmacokinetic of the therapeutic portion of fibrinogen (i.e., action of the therapeutic portion in the body over a period of time) may be governed by the following exemplary parameters: synthetic polymer:fibrinogen ratio, 3-D matrix formation, use of whole denatured fibrinogen or therapeutic portions of same, mode of administration. Each parameter can affect the biological activity of the release fibrinogen fragment, the release kinetics, the clearance rate from the body, and the immunogenic response of the therapeutic factor.

The following Table 1 provides exemplary formulations for various indications.

TABLE 1

| Release rate | Weeks following administration | Uses/ indications | Mode of administration | Formulation | PEG/denatured fibrinogen molar ratio |
|---|---|---|---|---|---|
| Slow | 10-150 | Bone, cartilage, cardiac, neural | Implantation, in situ polymerization | Hydrogel | 100:1-1000:1 |
| Intermediate | 2-10 | Bone, Muscle | Implantation, in situ polymerization | Hydrogel | 20:1-100:1 |
| Fast | 1-2 | Treatment of local infection in skin, bone, interstitium | In situ polymerization | Cross-linked | 10:1-20:1 |
| Immediate | 1 | Non-critical size injuries | In situ injection | Non-cross linked composition | 2:1-1000:1 |

The following describes the different parameters affecting pharmacokinetics:

3-D Matrix Formation—

Cross-linking the polymer-protein precursor molecules of the present invention may affect pharmacokinetics of the therapeutic portion. Such cross-linking can be performed in vitro, ex vivo and/or in vivo.

Cross-linking is performed by subjecting the precursor molecules to a free-radical polymerization reaction (i.e., a cross-linking reaction). Methods of cross-linking polymers are known in the art, and include for example, cross-linking via photoinitiation (in the presence of an appropriate light, e.g., 365 nm), chemical cross-linking [in the presence of a free-radical donor] and/or heating [at the appropriate temperatures. Preferably, cross-linking according to the present invention is effected by photoinitiation.

Photoinitiation can take place using a photoinitiation agent (i.e., photoinitiator) such as bis(2,4,6-trimethylbenzoyl) phenylphosphine oxide (BAPO) (Fisher J P et al., 2001; J. Biomater. Sci. Polym. Ed. 12: 673-87), 2,2-dimethoxy-2-phenylacetophenone (DMPA) (Witte R P et al., 2004; J. Biomed. Mater. Res. 71A(3): 508-18), camphorquinone (CQ), 1-phenyl-1,2-propanedione (PPD) (Park Y J et al., 1999, Dent. Mater. 15(2): 120-7; Gamez E, et al., 2003, Cell Transplant. 12(5): 481-90), the organometallic complex Cp'Pt(CH(3))(3) (Cp'=eta(5)-C(5)H(4)CH(3)) (Jakubek V, and Lees A J, 2004; Inorg. Chem. 43(22): 6869-71), 2-hydroxy-1-[4-(hydroxyethoxy)phenyl]-2-methyl-1-propanone (Irgacure 2959) (Williams C G, et al., 2005; Biomaterials. 26(11): 1211-8), dimethylaminoethyl methacrylate (DMAEMA) (Priyawan R, et al., 1997; J. Mater. Sci. Mater. Med. 8(7): 461-4), 2,2-dimethoxy-2-phenylacetophenone (Lee Y M et al., 1997; J. Mater. Sci. Mater. Med. 8(9): 537-41), benzophenone (BP) (Wang Y and Yang W. 2004; Langmuir. 20(15): 6225-31), flavin (Sun G, and Anderson V E. 2004; Electrophoresis, 25(7-8): 959-65).

The photoinitiation reaction can be performed using a variety of wave-lengths including UV (190-365 nm) wavelengths, and visible light (400-1100 nm) and at various light intensities. It will be appreciated that for ex vivo or in vivo applications, the photoinitiator and wavelengths used are preferably non-toxic and/or non-hazardous.

For example, the PEG-fibrinogen precursor molecule can be cross-linked by photoinitiation in the presence of Irgacure™ 2959 and a non-toxic UV light illumination (e.g., 5 minutes at 365 nm wavelength, 4-5 mWatts/cm$^2$ intensity).

It will be appreciated that although PEGylated fibrinogen molecules of the present invention are capable of being cross-linked without the addition of a cross-linking molecule, cross-linking according to the present invention can also utilize a molecule capable of cross-linking the polymer-protein precursors. Such cross-linking molecules can be for examples, PEG, PEG-DA, PEG multi-Acrylate, and/or PEG-VS.

Cross-linking may be effected such that the polymer-protein precursors of the present invention are solubilized in a water-based solution and such solutions are further subjected to cross-linking (e.g., using photoinitiation) to form a hydrogel scaffold. The hydrogel is subjected to the in vivo eroding conditions and releases the therapeutic portions of the denatured fibrinogen.

For example, a PEG-fibrinogen hydrogel was formed by mixing the PEGylated fibrinogen precursor molecules with the photoinitiation agent in the presence or absence of PEG-DA and exposing such a mixture to UV light. Briefly, the PEGylated fibrinogen precursors were solubilized in 1-ml of 50 mM PBS, pH 7.4 and 25° C. to achieve a final concentration of 10, 15, or 20% polymer-protein (w/v). The precursor solution also contained a PEG-DA cross-linking constituent at a molar ratio of 1:2 PEG-DA to functional groups on the PEGylated fibrinogen. The precursor solution was mixed with 10 µl of Irgacure™ 2959 photoinitiator solution (Ciba Specialty Chemicals, Tarrytown, N.Y.) in 70% ethanol (100 mg/ml) and centrifuged for 5 min at 14,000 RPM. The solution was then placed into Teflon tubes (5-mm diameter and 20-mm long) and polymerized under UV light (365 nm, 4-5 mW/cm$^2$) for 15 minutes according to published protocols (Lum L Y et al., 2003).

According to preferred embodiments of the present invention the hydrogel can be generated from PEGylated whole denatured fibrinogen or PEGylated fragmented fibrinogen (therapeutic portions). Generally, the molecular weight and length of the grafted PEG affects the degree of solubility of the PEGylated protein, i.e., higher length and/or molecular weight of PEG results in increased solubility of PEGylated protein. It will be appreciated that solubility of the PEGylated protein is also affected by the presence of whole or cleaved fibrinogen. Preferably, the concentration of the precursor molecules in the hydrogel is between 0.5 to 35%, more preferably, when PEGylated whole fibrinogen is used, the concentration of the precursor molecules in the hydrogel is between 0.5 to 5% (depending on the MW and length of the grafted PEG used to PEGylate the protein) and when PEGylated fragmented fibrinogen is used, the concentration of the precursor molecules in the hydrogel is between 5-35% (depending on the MW and length of PEG used to PEGylate the protein).

Synthetic Polymer:Fibrinogen Ratio— the molar ratio between the synthetic polymer (e.g., PEG) and fibrinogen of the present invention may affect pharmacokinetics of the composition. Thus, excess of the synthetic polymer would lead to binding of the polymer functional groups (e.g., PEG-DA) to all potential binding sites on the fibrinogen and, such that when cross-linked would result in a denser mesh with slower release pattern. On the other hand, binding of only two molecules of the synthetic polymer to each molecule of the protein (i.e., a 2:1 molar ratio) would result in fewer cross-linking sites and higher biodegradability of the scaffold. Thus, a higher molar ratio (i.e., excess of polymer) is expected to result in less biodegradability due to potential masking of protein degradation sites. Those of skills in the art are capable of adjusting the molar ratio between the synthetic polymer and the protein to obtain the desired formulation with the optimal physical and biological characteristics.

For example, since each fibrinogen molecule includes 29-31 potential sites which can bind to PEG, the PEG-fibrinogen precursor molecule can be prepared using a wide range of molar ratios. Preferably, the molar ratio used by the present invention is 2-400 (PEG) to 1 (fibrinogen), more preferably, the molar ratio is 30-300 (PEG) to 1 (fibrinogen), more preferably, the molar ratio is 100-200 (PEG) to 1 (fibrinogen), most preferably, the molar ratio is 130-160 (PEG) to 1 (fibrinogen). As is shown in Example 1 of the Examples section which follows, one preferable molar ratio between PEG-DA and fibrinogen is 145 (PEG) to 1 (fibrinogen). In the case where the molar ratio is greater than 29-31 (PEG) to 1 (fibrinogen), some of the PEG can be indirectly bound to the fibrinogen through fibrinogen-bound PEG molecules.

The fibrinogen used by the present invention can be whole denatured fibrinogen (i.e., un-cleaved) or fragmented fibrinogen, which can be obtained using, for example, CNBr cleavage.

Fibrinogen can be readily purified from human blood plasma using standard protein purification techniques. Purified components may be subject to anti-viral treatments. Heat-treatment and solvent/detergent treatments are both commonly used in the production of fibrinogen. Fibrinogen used in accordance with the present invention is preferably pure though other components may be present. Thus products may also contain tranexamic acid, aprotinin or factor XIII Fibrinogen is commercially available from Baxter and Omrix.

Routes of Administration—

Pharmacokinetics of the compositions of the present invention may be affected by the mode of administration. Hence pharmaceutical compositions which comprise the therapeutic portions of fibrinogen as an active ingredient or in a pro-drug form may be formulated for local or systemic administration.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

It will be appreciated that compositions of the present invention may be attached to-, or included in medical devices, such as for promoting wound healing following implantation or promoting cell settling on the implant.

Examples of medical devices which can be used in accordance with the present invention include, but are not limited to, intracorporeal or extracorporeal devices (e.g., catheters), temporary or permanent implants, stents, vascular grafts, anastomotic devices, prosthetic device, pacemaker, aneurysm repair devices, embolic devices, and implantable devices (e.g., orthopedic (e.g., an artificial joint) and orthodental implants), aneurysm repair devices and the like. Other devices which can be used in accordance with the present invention are described in U.S. Pat. Appl. No. 20050038498.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the disorder to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

To improve therapeutic efficacy, compositions of the present invention (e.g., hydrogel) may be loaded with any pharmaceutical agent of interest. Release rate is pharmacokinetically controlled by the above tailored formulations. Methods of loading hydrogels with pharmaceuticals are well known in the art [see for example, drug inclusion in bovine serum albumin hydrogels described in Gayet and Fortier (1995) Art. Cells. Blood Subs. And Immob. Biotech. 23(5), 605-611].

Thus, for example, compositions of the present invention may enclose components which are nonreactive to the composition (e.g., hydrogel). Examples of such nonreactive components may include drugs such as disinfectants, chemotherapeutics, antimicrobial agents, antiviral agents, hemostatics, antiphlogistics, anesthetics, analgesics, or nutritional supplements; biopolymers such as peptides, plasma derivative proteins, enzymes or mixtures thereof. In other words, components nonreactive to the hydrogel may be combined with the composition for hydrogel to provide stabilization or protection of these components. Such combined composition may be prepared, for example, by dissolving or suspending the nonreactive components in the aqueous medium to be used for gelation before effecting the gelation.

Compositions of the present invention may, if desired, be presented in a pack or dispenser device, such as an FDA-approved kit, which may contain one or more unit dosage forms (e.g., 100 mg) such as for personalized use containing the active ingredient (e.g., precursor molecules which are not yet cross-linked such as PEGylated denatured fibrinogen) and optionally sterile disposable means for delivery (e.g., syringe) and for illumination (e.g., illuminator covers). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Precursor Preparation

The blood-borne protein molecule fibrinogen is used to create a hybrid precursor molecule for tissue regeneration [Dikovsky et al., Biomaterials 27(8), 14-96-506, 2006; Almany and Seliktar, Biomaterials, 26(15), 2467-77, 2005]. Fibrinogen is the precursor to the commonly known blood clot protein, fibrin. The fibrinogen molecule contains a set of biological cell-signaling cues specific to cellular remodeling, including the cell-adhesive sequence Arg-Gly-Asp (RGD) and a protease degradation substrate [Herrick, Int J Biochem Cell Biol, 31(7) 741-6, 1999]. The fibrinogen molecules are transformed into a biosynthetic hybrid precursor using four sequential steps: 1) fibrinogen denaturation; 2) cleavage (optional); 3) PEGylation; 4) and 3-D matrix formation (optional). Each of these steps is detailed infra.

Figure 1B:
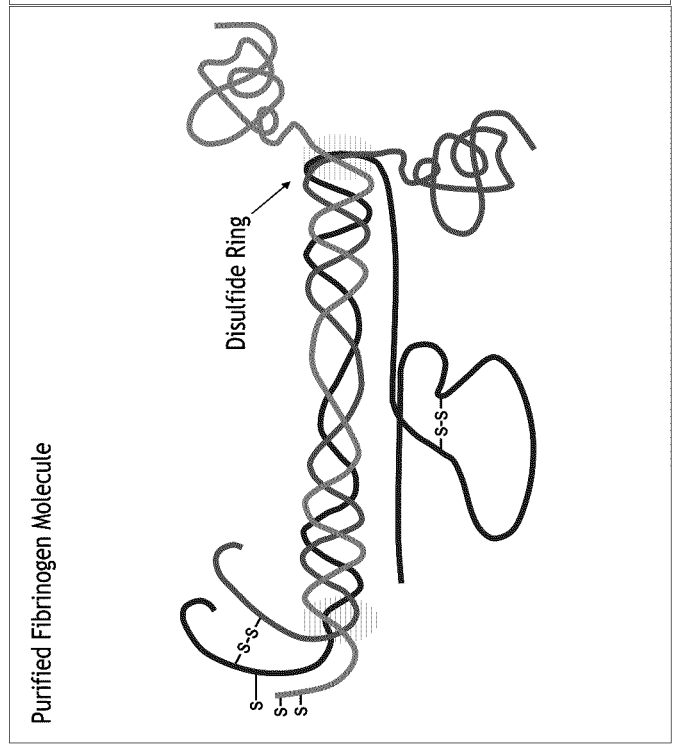
Figure 2A:
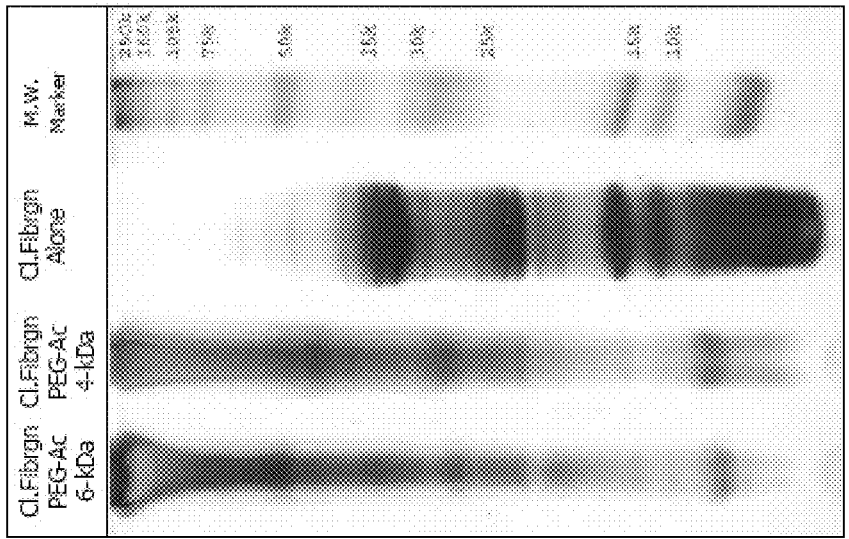
FIGS. 2*a-b* are protein SDS-PAGE images of denatured fibrinogen fragments prior to (FIG. 2*a*) and following (FIG. 2*b*) PEGylation. Note, denatured fibrinogen in the presence of PEG-OH migrates as three independent chains in the 50-60 kDa molecular weight range (FIG. 2*a*). Cleaved fibrinogen fragments are seen below the 50 kDa molecular weight range (FIG. 2*b*).
Figure 2B:
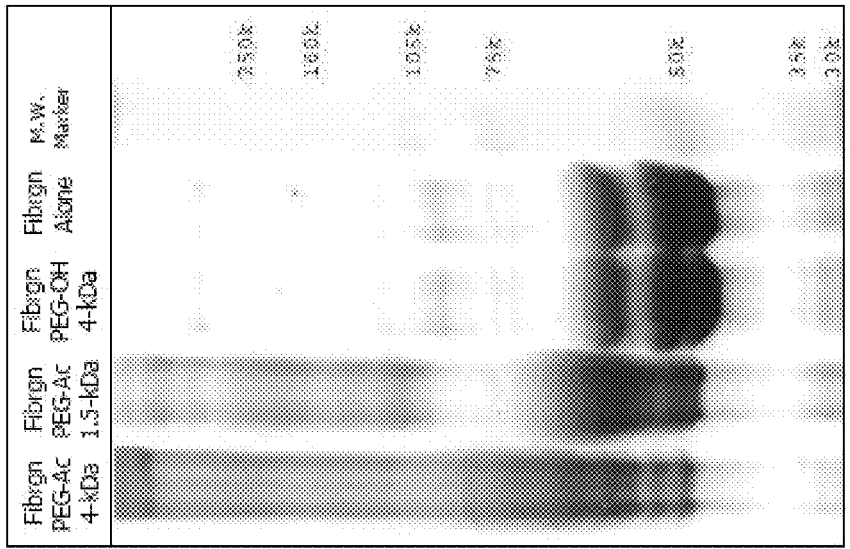

Step 1—Fibrinogen Denaturation: Denatured fibrinogen was prepared by incubating purified fibrinogen in a reducing solution containing a high excess of Urea. A denatured fibrinogen is represented in FIG. 1b. Briefly, purified bovine fibrinogen (Sigma-Aldrich, St. Louis, USA) was dissolved in 8 M urea—phosphate buffered saline (PBS) at a concentration of 3.5 mg/ml solution. Tris (2-carboxyethyl) phosphine hydrochloride (TCEP.HCl, Sigma, St. Louis, USA) was then added to the fibrinogen solution at a molar ratio 1.5:1 TCEP to fibrinogen cysteins. The 29-31 cysteine residues present in the sequence of the fibrinogen protein were denatured for 30 min in a stirred vessel at room temperature. The denatured fibrinogen fragments were visualized using SDS-PAGE and Coomassie®-blue staining (FIGS. 2a-b).

Step 2—Fibrinogen Cleavage: Following Fibrinogen denaturation, the solution was proteolytically cleaved using cyanogens bromine (CNBr). Basically, the denatured fibrinogen (Sigma, Steinheim, Germany) of step 1 was dissolved in a 70% formic acid solution containing 17 mg/ml cyanogen Bromide (Aldrich) and incubated overnight in the dark at 25° C. The cleaved fibrinogen fragments were then dialyzed in 50 mM phosphate buffered saline (PBS) at a pH=7.4 for 2 days at 4° C. with a twice-daily change of buffer to remove all the CNBr and formic acid from the solution. The dialyzed fragments were stored in PBS at 4° C. before the next step of the precursor preparation procedure. The fibrinogen fragments were visualized using SDS-PAGE to confirm degradation products (FIG. 2b).

Figure 3B:
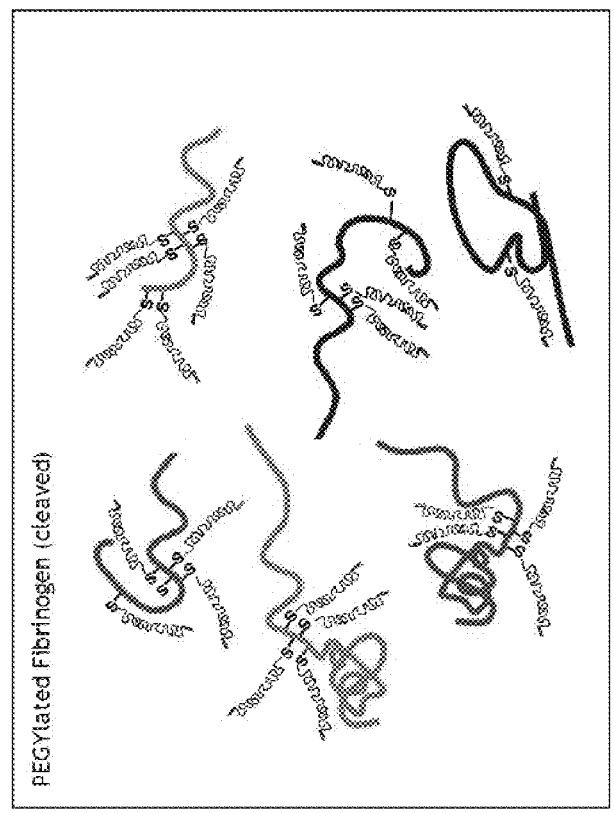
FIGS. 3a-b are schemes showing PEGylated fibrinogen (whole, FIG. 3a) and fibrinogen degradation products (cleaved, FIG. 3b). The bound polymer can be monofunctional, difunctional (shown), or multifunctional. The remaining reactive groups on the polymer can be used to covalently bind the denatured fibrinogen degradation products or whole denatured fibrinogen into a 3-D matrix for local implantation.
Figure 3A:
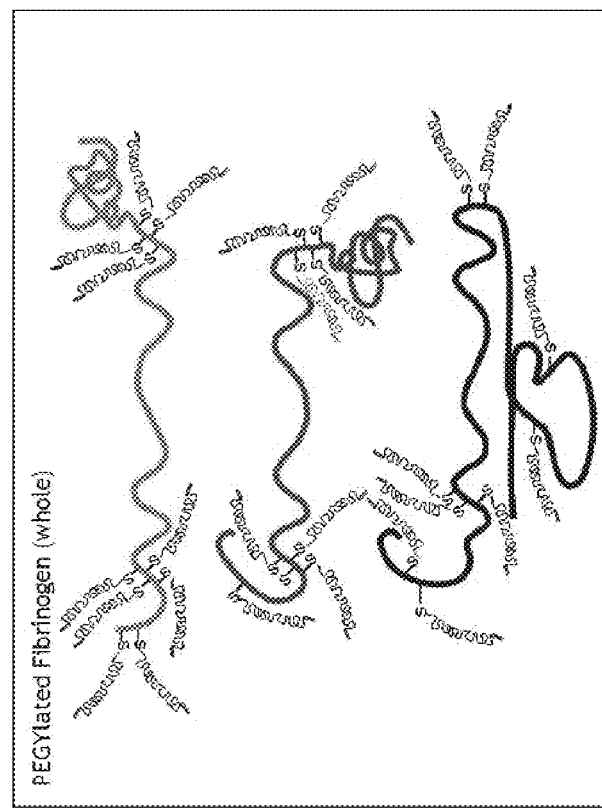

Step 3—Denatured fibrinogen PEGyaltion: Cleaved Fibrinogen or uncleaved whole fibrinogen was bound to monofunctional or multifunctional poly(ethylene glycol) (PEG) polymer using a Michael type addition reaction between the functional end groups on the PEG polymer and the reduced thiols on the denatured fibrinogen product. The PEGylation reaction scheme effected herein used linear PEG diacrylate (PEG-DA)(6-kDa or 10-kDa, Fluka Chemika GmbH, Buchs, Switzerland). A solution of PEG-DA (280 mg/ml) in 50 mM PBS and 8M urea was added and reacted for 3 hours with cleaved or uncleaved denatured fibrinogen (of step 1 and/or 2). The molar ratio of PEG to fibrinogen cysteins is 5:1 or more using linear PEG-DA, 6-kDa and 10-kDa. The PEGylated protein was precipitated by adding 4 volumes of acetone (Frutarom, Haifa, Israel). The precipitate was redissolved at 10 mg/ml protein concentration in PBS containing 8 M urea and dialyzed against 50 mM PBS at 4° C. for 2 days with twice-daily changes of PBS (Spectrum, 12-14-kDa MW cutoff). To establish the total PEG-fibrinogen concentration, 0.5 ml of the precursor solution were lyophilized overnight and weighed. The net fibrinogen concentration was determined using a standard BCA™ Protein Assay (Pierce Biotechnology, Inc., Rockford, Ill.) and the relative amounts of total PEGylated product (dry weight) to fibrinogen content (BCA™ result) were compared. A PEGylation efficiency scale was used to determine percent PEGylation of the protein product. The scale assumes 100% PEGylation when all 29 free thiols on the fibrinogen molecules (166 kDa total) are bound to the functionalized PEGs. Schematic illustrations of PEGylated fibrinogen are shown in FIGS. 3a-b.

Step 4—3-D matrix formation: The polymer-modified denatured fibrinogen protein (cleaved or whole) can be administered directly by injecting the precursors locally or systemically, or alternatively, by creating a 3-D matrix for sustained local delivery of the fibrinogen degradation products to the surrounding tissue in a site-specific treatment application. The use of a 3-D matrix for this purpose is done by immobilizing the PEGylated fibrinogen to an existing biocompatible matrix, or else by making a 3-D hydrogel matrix from the PEGylated precursors using polymerization of the additional reactive end groups on the polymer.

The following provides an example using photoreactive chemistry to create denatured PEGylated fibrinogen hydrogels. PEG-modified denatured fibrinogen (cleaved or whole) is formed into a solid polymer network by cross-linking between the free functional groups on the PEG-DA. These hydrogels are made from a precursor solution of denatured PEGylated fibrinogen by a radical chain polymerization reaction of acrylate end groups. The purified PEGylated precursor solution (2-3% PEGylated polymer—w/v) contains about 2 μM free acrylate groups for cross-linking. Additional PEG-DA (6-kDa or 10-kDa) can be added to increase cross-linking density of the PEGylated protein network as well as to minimize steric hindrance that may result in poor gelation (Gnanou et al, Macromolecules, 20, 1662-1671, 1987).

Figure 4B:
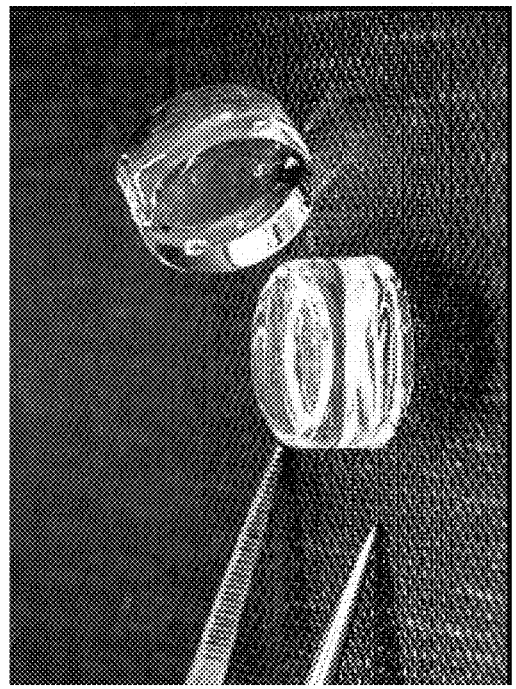
FIGS. 4a-b show the creation of a matrix from denatured PEGylated fibrinogen showing the molecular architecture schematically illustrated in FIG. 4a and the macroscopic appearance of FIG. 4b.
Figure 4A:
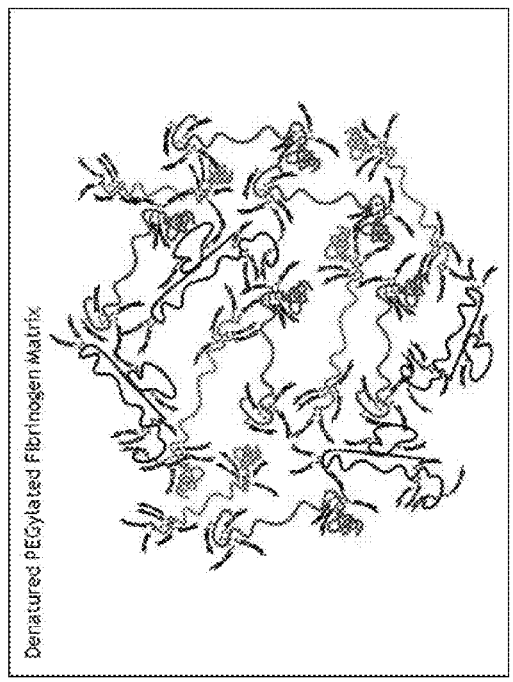

Briefly, the precursor solution was mixed with 1% (v/v) photoinitiator stock solution made of 10% w/v Irgacure™ 2959 (Ciba Specialty Chemicals, Tarrytown, N.Y.) in 70% ethanol and deionized water. The solution was placed under a UV light (365 nm, 100 mW/cm$^2$) for 5 min to polymerize. The molecular architecture and appearance of the hydrogels are shown in FIGS. 4a-b.

Example 2

Denatured PEGylated Fibrinogen Degradation

The degradation of denatured or fragmented PEGylated fibrinogen into PEGylated fibrinogen degradation products was verified experimentally using an in vitro degradation assay. Basically, PEGylated denatured/fragmented fibrinogen fragments are formed into a matrix to recreate a 3-D matrix which can be implanted into a site-specific defect.

Several variations of the PEGylated fibrinogen fragments are used in these experiments, including cleaved and whole protein with either 6-kDa or 10-kDa PEG-DA attached to the protein. Protease degradation of the denatured PEGylated fibrinogen is measured by colorimetrically assessing the release of the PEGylated fibrinogen degradation products into the supernatant during the course of the experiments.

Cylindrical plugs are cast in 5 mm diameter silicon tubes from 100 µl aliquots of PEG-fibrinogen precursor solution containing photoinitiator. The degradation is quantified by labeling the PEGylated fibrinogen with eosin-Y, which binds with high affinity to the fibrinogen, and quantifying the release of the fibrinogen resulting from enzymatic dissolution from the 3-D matrix. As the soluble fibrinogen degradation products are dissociated from the matrix, these released fragments are quantified by spectrophotometric measurements in an overlaying buffer solution.

Materials and Experimental Results

Casting of PEGylated Fibrinogen— effected as described above.

Fibrinogen Degradation—

PEGylated fibrinogen 3-D samples were stained in 5 mg/ml eosin-Y solution (Sigma-Aldrich, St. Louis, USA) for 2 days, washed, and transferred into 2 ml of either 0.01 mg/ml trypsin or 0.1 mg/ml collagenase solution (Worthington, St. Louis, USA) containing 50 mM PBS and 0.1% sodium azide. Absorbance values are measured spectrophotometrically at 516 nm every 30 min for 3 hours. After the last time point, each hydrogel was hydrolytically dissociated, and absorbance values were recorded as 100% degradation.

Results

FIGS. 5a-d depict the results from degradation experiments demonstrating that the percent degradation of PEG-fibrinogen precursors (i.e., ratio of release PEG-fibrinogen to total PEG-fibrinogen) was affected by the molecular weight of the grafted PEG, the composition of PEG to fibrinogen, and the molecular configuration of the denatured fibrinogen (whole or cleaved). The degradation of the PEG-fibrinogen precursors in collagenase (0.1 mg/ml, FIGS. 5c-d) or trypsin (0.01 mg/ml, FIGS. 5a-b) is shown.

The kinetics data reveals that precursors made with 10-kDa PEG, are released faster from the matrix than precursors made with 6-kDa PEG. Addition of PEG-DA to the precursor solution resulted in significantly slower degradation kinetics (n=5, p<0.01). Changing the PEG molecular weight from 6-kDa to 20-kDa resulted in accelerated degradation in the presence of 0.05 mg/ml trypsin (n=6, p<0.05, data not shown). The PEGylated precursor responsiveness to differing enzyme concentrations was assessed by measuring degradation in serial dilutions of collagenase or trypsin following 30 minutes of incubation (not shown). The results from these experiments confirm dose-dependent relationship between of the degradation kinetics of the PEGylated precursors and the enzyme concentrations. The results were also verified by degrading PEGylated fibrinogen fragments and analyzing them using SDS-PAGE (data not shown) which revealed smaller fragments of PEGylated degradation products compared to the non-degraded PEGylated precursors.

Example 3

Tissue Culture Assay

The protease-mediated release of the denatured PEGylated fibrinogen products from intact 3-D materials may have a profound chemotactic effect on in vitro tissue cultures of various types. It is assumed that when released from the 3-D matrix, the denatured PEGylated fibrinogen degradation products may facilitate the chemotactic invasion of cells, including vascular smooth muscle cells, chondrocytes, and embryonic stem cells, into the 3-D matrix containing the bound PEGylated fibrinogen. Therefore, the chemotactic potential of the denatured PEGylated fibrinogen degradation products was assayed by an in vitro tissue culture assay designed in part for this task.

Chemotaxis Assay—

A cell invasion assay was employed using smooth muscle tissue encapsulated by a PEGylated fibrinogen matrix (10 kDa PEG). Dense tissue constructs composed of smooth muscle cell-seeded collagen gels placed inside PEG-fibrinogen hydrogels. The smooth muscle tissue constructs were made from a solution of 5×DMEM, 10% FBS, reconstituted type-I collagen solution in 0.02 N acetic acid (2 mg/ml), and 0.1 M NaOH with dispersed smooth muscle cells ($3 \times 10^6$ cells/ml, cell were isolated from bovine aortic tissue explants according to standard protocols [Seliktar et al, Ann Biomed Eng, 28(4), 351-62, 2000]. The collagen gels were placed in 300 µl of PEG-fibrinogen precursor solution (with photoinitator) in a 48-well plate and exposed to UV light for 5 minutes. The polymerized hydrogels encapsulated the tissue during the gelation process. The encapsulated tissue constructs were supplemented with 600 microliters of culture medium containing DMEM (Gibco), Pen-strep, and fetal bovine serum (FBS, Gibco). The constructs were placed in a controlled temperature and $CO_2$ incubator and medium was replenished every other day. The cells were imaged daily using a phase contrast microscope to determine the level of cell migration from the edge of the tissue and into the PEG-fibrinogen hydrogel. Histological staining for cell morphology [Hematoxylin and Eosin (H&E)] were performed to assess the morphology of invading cells.

Cartilage explant experiments were performed using similar methods as with the smooth muscle tissue. In this case 1-mm slices of articular cartilage explants, were isolated from sheep knee joints and immersed in the precursor solution prior to being polymerized with UV light (365-nm, 700 µW/cm$^2$). The encapsulated explants were cultivated with twice-weekly replenishment of medium and periodic imaging as detailed above. Histological staining for proteoglycans (Safranin-O), cell morphology (H&E), and immuno-staining for type I and type II collagen were performed to assess the phenotype of invading chondrocytes and the explanted specimen.

Results

FIGS. 6a-j show cellular invasion from vascular tissue into PEG-Fibrinogen containing hydrogel matrix. Initially, the smooth muscle cells were contained within the collagen gel construct (FIG. 6a). Several hours following casting, the cells began to proteolytically degrade the matrix and release PEGylated fibrinogen degradation products. The chemotactic effect of the peptides caused a massive cellular invasion into the dense PEG-fibrinogen matrix surrounding the tissue mass (FIG. 6b), which lasted for the duration of the culture period as more PEGylated fibrinogen was proteolytically degraded by the cell-secreted enzymes (FIG. 6c). Of note, during the first 96 hours of culture, the rate of cellular degradation and invasion was nearly constant and proportional to the molecular weight of the PEG-fibrinogen precursors (data not shown). Following this period, the degradation and invasion into the matrix was more aggressive as indicated by a sharp increase in the rate of cellular invasion after one week (91% increase, n=5, p<0.01, FIG. 7a). Overall, the rate of cellular degradation and invasion into 10-kDa PEG-fibrinogen hydrogels was significantly higher than the rate of degradation and invasion into 6-kDa hydrogels (n=4, p<0.05) (FIG. 7b). The additional PEG-DA used to polymerize the hydrogel network significantly altered the rate of cellular degradation and invasion into the denatured PEGylated fibrinogen containing matrix (FIGS. 6a-j, FIG. 7a-b).

Other tissue types demonstrated similar responses when encapsulated in the above degradable matrix. Studies using both embryonic stem cells and cartilage tissue explants exemplified the chemotactic response of both tissue types to the PEGylated degradation products (FIGS. 7c-d, respectively).

Example 4

In Vivo Osteogenesis Mediated by PEGylated Fibrinogen Degradation Products

The osteoinductive properties of denatured PEGylated fibrinogen degradation products in osseous regeneration were studied in a site-specific bone defect.

Materials and Experimental Procedures

Implant Fabrication:

Acellular cylindrical plugs were cast in 3-mm diameter silicon tubes using 88 µl aliquots of PEG-fibrinogen precursor by a photopolymerization reaction of acrylate end groups. Additional PEG-DA (3% or 5% w/v) was added to the precursor solution in order to reduce the susceptibility of the PEGylated fibrinogen backbone to proteolytic degradation (Table 1, below). The final ratio of PEG to fibrinogen monomer was 25:1, 100:1, and 150:1 for the 0% PEG-DA, 3% PEG-DA, and 5% PEG-DA, respectively. These different compositions correspond to fast, intermediate and slow degrading hydrogels (respectively) as indicated in Table 1 below. The precursor solution was mixed with 0.1% (v/v) photoinitiator stock solution consisting of 10% w/v IRGACURE™ 2959 (2-hydroxy-1-[4-92-hydroxyethoxy)phenyl]-2-methyl-1-propanon; generously donated by Ciba Specialty Chemicals, Tarrytown, N.Y.) in 70% ethanol and deionized water. The solution was placed under a UV light (365 nm, 40-50 mW/cm$^2$) for 5 min to polymerize. The pre-cast hydrogels were stored in 50 mM PBS containing 2% penicillin-streptomycin (Biological Industries, Israel) for 5 hrs prior to implantation.

Rat Implantation—

Approval of the Institutional Review Board of the Rappaport Faculty of Medicine of the Technion, Israel Institute of Technology was obtained prior to initiation of the performed experiments and all experiments were performed in accordance with the guidelines set out by the Technion animal care committee. Female Sprague-Dawley rats (32 animals altogether) aged 3 to 4 months and weighting about 250 gm) were adapted to cage life for 5 days prior to the surgery. The weight of the animal was monitored during this period to ensure stability and proper adaptation. The animals were fed regular lab chow and had access to tap water ad libitum. They were anesthetized with a combination of Ketamine 120 mg/kg and Xylazine 17 mg/kg. During the surgical procedure the animal was placed on a warm plate to maintain body temperature (and prevent hypothermia). The right tibia was shaved and wiped with polydine tincture solution. The mid-portion of the right tibia was exposed from the anterior medial side by longitudinal incision. An external fixation device was placed proximal and distal to the mid-section of the tibia according to published protocols [Srouji et al, Cell Tissue Bank, 5(4), 223-30, 2004]. Briefly, two needles were drilled into the proximal (21 G) and distal (23 G) segments of the tibia and connected to two external fixation apparatuses so as to stabilize the bone (FIGS. 8a-d). A 7-mm gap was excised using a high-speed disk saw in the portion between the proximal and distal needles of the fixation devices. The ipsilateral fibula was left intact. A PEG-fibrinogen plug (3-mm diameter and 7-mm long) was inserted into the site of the defect and the surrounding periosteum as well as the subjacent fibrous tissue were wrapped around and sutured to secure the plug in place (FIG. 8d). The incisional wound was sutured with a nylon surgical thread. The rats were given prophylactic antibiotics (ampcillin 0.1 gr/100 g). They were x-rayed shortly after the surgery and thereafter were evaluated at weekly intervals by x-ray screening. They were housed in spacious cages so as to allow relative free ambulation during the entire postoperative follow-up period. At the end of the 5 week evaluation period, the rats were sacrificed with $CO_2$ and the right tibial bones were harvested for histological evaluation.

Results

Hydrogel comprising PEGylated fibrinogen with various degrees of proteolytic resistance based on poly(ethylene glycol) and fibrinogen composition were designed for slow, intermediate, and fast release kinetics of the degradation products. The hydrogels were implanted into site-specific defects of rats' tibiae without additional osteoinductive factors with the rational that the matrix will displace the normal fibrin clot while sustaining a similar healing effect in the defect site for a longer duration by releasing the denatured PEGylated fibrinogen degradation products. Histological and x-ray results described in details hereineblow have confirmed that following 5 weeks of implantation, the extent and distribution of newly formed bone in the defect strongly correlates with the erosion pattern of the implanted material and subsequent release of degraded PEGylated fibrinogen to the local tissue environment. When compared to nonunions in untreated control animals, the rats implanted with the intermediate-degrading PEG-fibrinogen materials displayed osteoneogenesis. These data support the suggestion that the release of denatured PEGylated fibrinogen degradation products provides inductive properties. In this site-specific bone defect model, the sustained release of denatured PEGylated fibrinogen degradation products facilitates the osteogenic response in the injury site.

TABLE 1

Summary of Treatment Cohorts

| Group | Degradation | Composition PEG:Fibrinogen ratio | Degradation Rate in 0.01 mg/ml Trypsin (% Wt Loss/min$^{1/2}$) | Degradation Rate In 0.1 mg/ml Collagenase (% Wt Loss/min$^{1/2}$) |
|---|---|---|---|---|
| Control | N/A | Empty gap | N/A | N/A |
| 1 | Fast | 25:1 | 6.960 | 7.878 |
| 2 | Intermediate | 100:1 | 1.168 | 1.928 |
| 3 | Slow | 150:1 | 0.292 | 0.351 |

Specific analyses effected to substantiate the osteoindcutive effect of the compositions of the present invention Histological Analysis:

Following a final radiographic evaluation, the right tibia of each rat was carefully excised in its entirety. The samples were fixed in buffered, neutral 10% formalin solution for 10 days and then decalcified in 10% formic acid for 10 days. The specimens were trimmed so as to include the implant site and the adjacent bone tissue on either side of the defect. After rinsing in PBS, the specimens were dehydrated in increasing concentrations of ethanol in deionized water (70% to 100%). Specimens were embedded in extra-large paraffin blocks, which were sectioned at 6 µm, fixed on poly-1-lysine coated glass slides, and stained with hematoxylin and eosin (H&E).

Figure 9A:
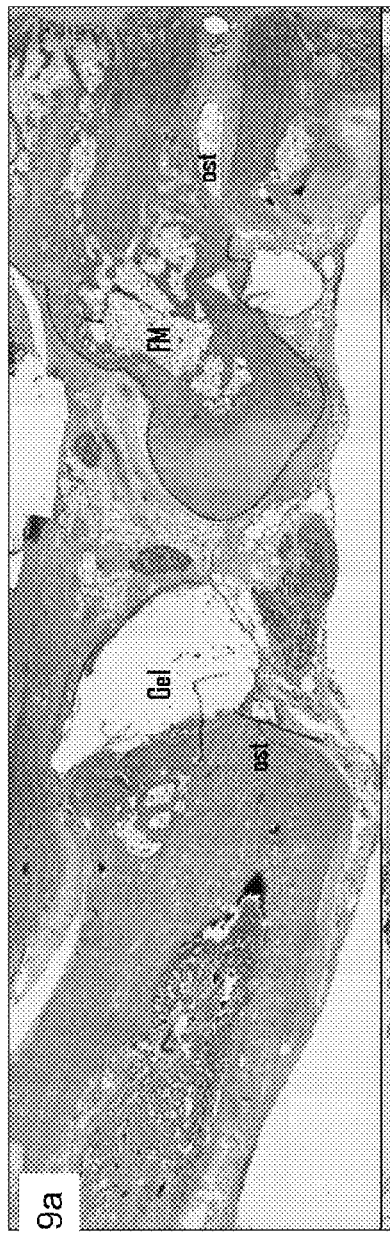
FIGS. 9a-c are photomicrographs depicting longitudinal sections of intermediate-degrading hydrogel-treated tibial defects 5 Weeks post-operation. The extent of regenerated bone in the site-specific defect ranged from partial (FIGS. 9a-b) to total bridging (FIG. 9c) of the defect osteotomies (ost), and highly depended on the erosion pattern of the hydrogel material (Gel). Remnants of the gel gave way to regenerated bone (dashed line), having typical lamellar-fibred pattern of mature osseous trabeculae and fatty marrow (FM). The sections were stained with hematoxylin and eosin (H&E)
Figure 9B:
Figure 9C:
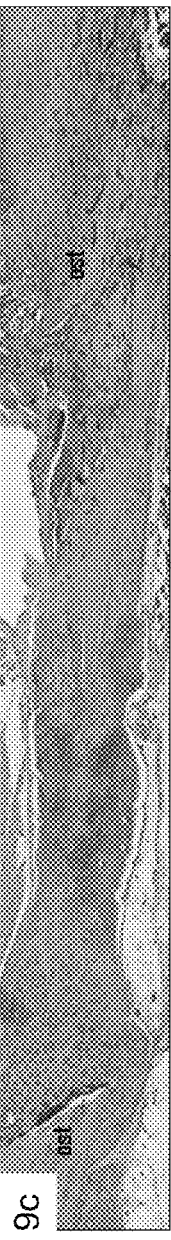
Figure 15B:
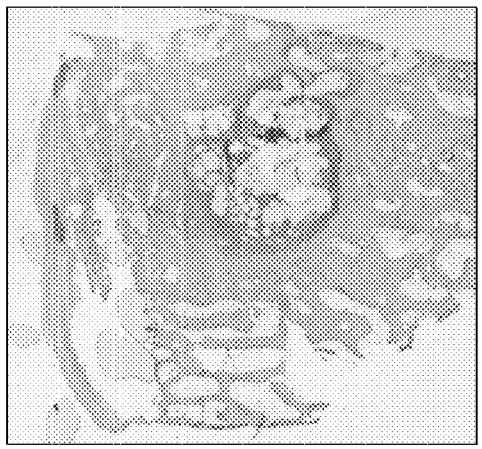
FIGS. 15a-d are longitudinal histological sections of the 6-mm osteochondral defects 4 months following implantation stained for Type I collagen using monoclonal antibodies. The defects are either left empty (FIG. 15a empty control) or treated with hydrogels of denatured PEGylated fibrinogen (FIGS. 15b-d) with different concentrations of PEG and fibrinogen in each treatment. Histology is shown for treatments with (FIG. 15b) 150:1 molar ratio of PEG to fibrinogen, (FIG. 15c) 200:1 molar ratio of PEG to fibrinogen, and (FIG. 15d) 350:1 molar ratio PEG to fibrinogen in the defect site. All treated defects showed new bone staining positive for Type I collagen (brown color).
Figure 15D:
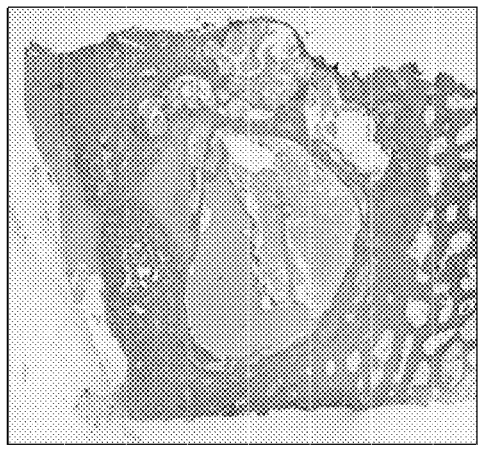
Figure 15A:
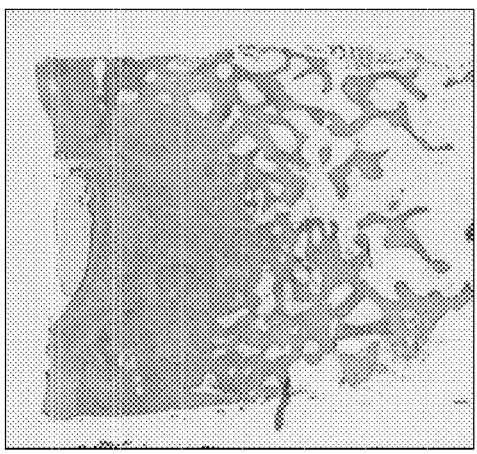
Figure 15C:
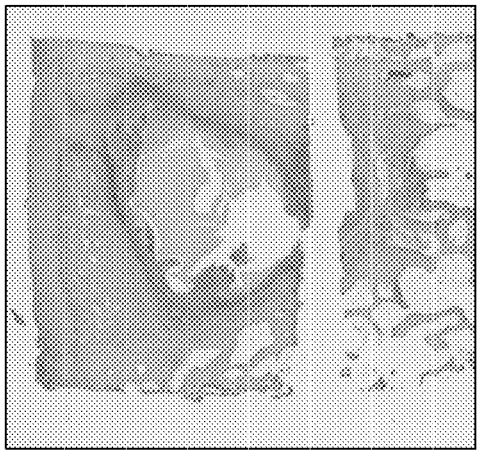

Resulting Osteogenesis:

Newly formed bone in the site-specific defects of the tibiae was radiographically observed as early as three weeks postoperatively. When compared to control rats, large amounts of new bone were apparent in the defects of the treatment-2 animals by 5 weeks (data not shown). This contrasted with the lack of radiographically detectable bone in the defects of the treatment-1 (fast degrading), treatment-3 (slow degrading) and control rats. The histological examination confirmed that the rats treated with the intermediate-degrading treatment 2 exhibited the most extensive and widespread osteoneogenesis in and nearby the defect site. The longitudinally, H&E-stained sections of the tibiae revealed that the extent of regenerated bone in the site-specific defects ranged from partial to total bridging of the gap (FIGS. 9a-c). Osteoneogenesis was observed at both the endosteal and subperiosteal aspects. When observed under polarized light, the birefringent pattern of the preexisting lamellar-fibered cortical bone sharply contrasted to that of the woven-fibered boney trabeculae, characteristic of newly deposited osseous tissue. The newly formed subperiosteal bone at the osteotomy sites was contiguous with the boney trabeculae, which were for the most part rimmed by cuboidal osteoblasts on their inner front. The endosteally formed bone was as well continuous with newly formed trabeculae, which extended into the defect site. Randomly scattered adipocytic islands were present in between the trabeculae of the newly formed woven-fibered bone. In but a few samples, the medullary cavity contained some fibrous tissue proximal to the osteotomy site.

In those cases in which there was total osseous bridging of the site-specific defect, the implant had been entirely resorbed and replaced by lamellar-fibered bone with an atypical pattern of Haversian, essentially, osteonal bone. The newly formed bone was uninterrupted from one end to the opposite end of the osteotomies (FIG. 9c), consisting of birefringent, lamellar-fibered, compacta-type bone with a moderate number of vessels within the Haversian system (data not shown), characteristic of mature bone. In those instances in which there was but a partial bridging of the defect, there was often endochondral ossification of cartilaginous islets. To exemplify, FIG. 10a illustrates a typical endochondral cap at the medial aspect of the regeneration front: Hypertrophic chondrocytes were focally present in the cartilaginous cap, which was enclosed by a thin, perichondrium-like fibrous tissue with parallel-oriented mature fibrocytes at its leading edge (FIGS. 10a-b).

Mechanism of Neoosteogenesis—

As shown above only the intermediate degrading PEG-fibrinogen hydrogel treatment (treatment-2) caused extensive new bone formation at the site of the boney defect. Nevertheless, judging from just the histological findings it is clear that the PEGylated fibrinogen material is endowed with osteoinductive properties and that the macrophages that erode the denatured PEGylated fibrinogen containing matrix slowly release osteoinductive denatured PEGylated fibrinogen degradation products to act as an eroding front for osteoneogenesis to occur in as much as the gels slowly give way for the newly generating bone. There is consistency with the observations that faster degrading hydrogels do not provide synchronized release with the natural healing rate in a rat site-specific bone defect, which typically requires 4 to 5 weeks to heal completely. It is important to note that in this study, the gel composition was deliberately chosen to coincide with the optimal degradation rate and healing kinetics of this type of injury. Even though slow and fast degrading gels are suboptimal for this type of injury, it is the ability to regulate the degradation and release of the PEGylated fibrinogen degradation products that allows the present this technology to treat any number of different type of injury in humans.

It was observed that the fragments released from the PEG-fibrinogen hydrogel facilitate a prolonged osteogenic response within the site-specific defect. In particular, a sustained release of the denatured PEGylated fibrinogen degradation products explain the extent of the oesteogenic response in the treatment of group 2 rats. There is ample evidence that fibrinogen and fibrin degradation products are potent agonist of wound healing [Thompson et al, J Pathol, 165(4), 311-8, 1991; Rybarczyk et al, Blood, 102(12), 4035-43, 2003], especially as concerns endothelial cells [Lorenzet et al, Thromb Haemost, 68(3), 357-53, 1992; Bootle-Wilbraham et al, Angiogenesis, 4(4), 269-75, 2001] and fibroblasts [Gray et al, Am J Respir Cell Mol Biol, 12(6), 684-90, 1995; Gray et al, J cell Sci, 104(Pt2), 409-13, 1993]. In fact, fibrin has been evidenced to induce an osteogenic response in bone defects filled with osteoconductive materials [Le Guehennec et al, J Mater Sci Mater Med, 16(1), 29-35, 2005; Abiraman et al, Biomaterials, 23(14), 3023-31, 2002; Kania et al, J Biomed Mater Res, 43(1), 38-45, 1998]. Moreover, if fibrinogen fragments do not possess osteoinductive qualities, we would expect a similar outcome to that demonstrated by other researchers who utilize the inert biomimetic ingrowth matrices without added growth factors. Pratt et al. have reported that eroding fibrin-mimetic hydrogels are unable to support new bone formation when occupying a size-specific calvarial defect in the absence of the osteoinductive BMP-2 [Pratt et al, Biotechnol Bioeng, 86(1), 27-36, 2004]. Likewise, Lutolf et al. have demonstrated similar results employing a collagen-mimetic biosynthetic ingrowth matrix without osteoinductive BMP-2 [Lutolf et al, Nat Biotechnol, 21(5), 513-8, 2003]. In comparison, the extent of osteoneogenesis using PEG-fibrinogen containing hydrogels without added osteoinductive growth factors can only be explained by an osteoinductive role of the PEGylated fibrinogen degradation products in as much as it is unlikely that the PEG constituent has osteoinductive qualities.

The unprecedented osteoneogenesis observed in this study is attributed to the released fragments of PEGylated fibrinogen degradation products and not necessarily to the intact matrix. A sustained presentation of mildly osteogenic PEGylated fibrinogen fragments could account for the prolonged osteogenic response over the 5 weeks of the healing period. This explanation is consistent with the fact that most of the osteoneogenesis in the treatment-2 defects occurs at least several hundred microns from the eroding surface of the hydrogels (FIG. 11a), the latter being consistently surrounded by an inflammatory infiltrate. Even the slow degrading hydrogels (treamtnet-3) induce some mild osteogenic response around the implant, presumably because of the released fragments of PEGylated fibrinogen (data not shown). From this point of view, there is no evidence of osteoneogenesis in the fast degrading hydrogel-treated animals (treatment-1), suggesting that rapid dissolution of the PEGylated fibrinogen fragments does not enable adequate new bone formation.

Example 5

In Vivo Chondrogenesis Mediated by PEGylated Fibrinogen Degradation Products

The osteoinductive properties of denatured PEGylated fibrinogen degradation products in cartilage regeneration were studies in a critical size osteochondral defect.

Materials and Experimental Procedures

Precursor Fabrication—

PEG-fibrinogen precursor was made from PEGylated fibrinogen according to the method detailed above. The implant solution was modified with additional PEG-DA in order to reduce the susceptibility of the PEGylated fibrinogen backbone to proteolytic degradation. The final ratio of PEG to fibrinogen monomer used was 150:1, 200:1, and 350:1. The aliquots of PEG-fibrinogen precursor were mixed with 0.1% (v/v) photoinitiator stock solution including 10% w/v Irgacure™ 2959 (generously donated by Ciba Specialty Chemicals, Tarrytown, N.Y.) in 70% ethanol and deionized water. The polymerization of the solution was tested under UV light (365 nm, 40-50 mW/cm$^2$) for a 5 min duration to determine if the solution polymerizes prior to implantation. Once polymerization was verified, the precursor solution was ready for in situ polymerization. In the osteochondral defect model, the implant is polymerized directly in the 6-mm defect using a UV source and light guide (FIGS. 12a-d).

Sheep Implantation:

Adult, skeletally mature sheep (weighing on average 70 kg) were adjusted to cage life one week prior to operation. Following a 24-h fast and pre-medication by i.v. infusion of ketamine-Hcl 10 mg/kg and xylazine 0.05 mg/kg, induction by i.v. administration of propofol 4-6 mg/kg, the animal was intubated. After intubation, including maintenance by inhalation of isoflurane 1.5-2% and ventilated by positive pressure of 100% $O_2$ by volume control, a bolus of 0.1 mg fentanyl was administered to the animal immediately prior to surgery. Postoperative analgesis by p.o. tolfine 2-4 mg/kg×3/d was conducted. The animals received 2.5 g metamizol and 1 g cefazoline twice daily until the third postoperative day. The experiments were performed on the right stifle joint of the hind leg of the sheep. The leg was sterilely draped and opened by a parapatellar anterolateral approach. The paterlla was dislocate medially, and the femoral condyle was exposed. Using a 6-mm custom made punch and drill tool, two defects, 1 and 2.5 cm distal from the intercondylar notch, were introduced in the weight bearing zone of the femoral condyles (FIG. 12a). The defects were created with the punch and both the subchondral bone and cartilage were completely removed with the drill bit. There was some intraoperative bleeding from the subchondral bone which was subdued using a sterile gauze. Into the non-bleeding defect sites the PEG-fibrinogen solution was sterilely injected and polymerized in situ using a hand-held, UV light source (FIG. 12d). Wound closure was then performed in layers. An external plaster (Scotch/Soft Cast, 3M HealthCare, St. Paul, Minn., USA) was applied on the stifle and ankle joint for 5 days. The animals' cage activity was limited in order to reduce joint loading. After the removal of the plaster, the sheep was allowed to move freely, and given a balanced diet twice a day. At the end of the 4-month evaluation period, the animals were sacrificed and the stifle joints of the hind leg was harvested for gross observation, histology, and immunohistochemistry. Following sacrifice, the distal femur was removed and placed in 10% neutral buffered formalin. After 24 h, the areas of condyles containing the defects were dissected and placed back in 10% formalin for 4 days. The decalcified specimens were embedded in paraffin and sectioned to 4-mm-thick slices.

Results

Osteochondral defects treated with PEGylated fibrinogen hydrogels exhibited regeneration of articular cartilage as observed by gross observation after 4 months (FIGS. 13a-d). FIG. 13a-b show the four defects on the day of operation, in the patellar notch (FIG. 13a) and in the condyle (FIG. 13b). After four months, the same defects are shown in the patellar notch (FIG. 13c) and the condyle (FIG. 13d). Only the medial patellar notch defect (FIG. 13c, right) did not exhibit new cartilage formation. All the other defects, which were treated, had new cartilage growing on the joint surface.

Figure 16B:
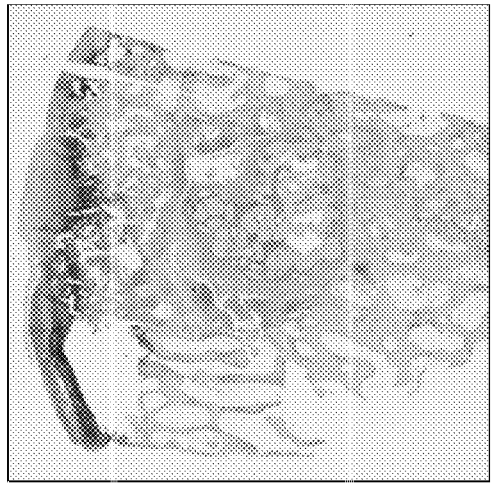
FIGS. 16a-d are longitudinal histological sections of the 6-mm osteochondral defects 4 months following implantation stained for proteoglycans using safranin-o stain. The defects are either left empty (FIG. 16a empty control) or treated with hydrogels of denatured PEGylated fibrinogen (FIGS. 16b-d) with different concentrations of PEG and fibrinogen in each treatment. Histology is shown for treatments with (FIG. 16b) 150:1 molar ratio of PEG to fibrinogen, (FIG. 16c) 200:1 molar ratio of PEG to fibrinogen, and (FIG. 16d) 350:1 molar ratio PEG to fibrinogen in the defect site. All treated defects showed new cartilage staining positive for proteoglycans (red color), compared to empty control which does not stain positive. The proteoglycan staining using safranin-o (red stain is positive) confirms the presence of glycosaminoglycans (GAG) in the newly formed cartilage surface.
Figure 16D:
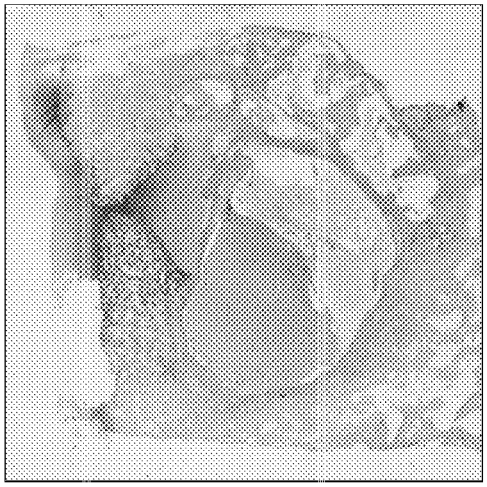
Figure 16A:
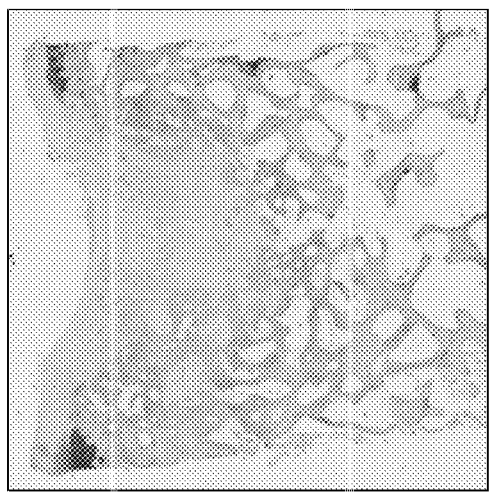
Figure 16C:
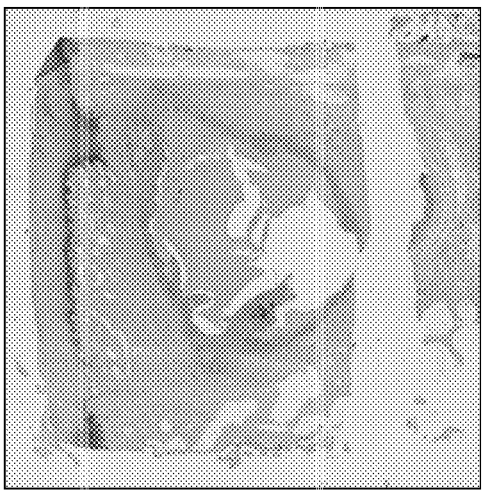
Figure 17B:
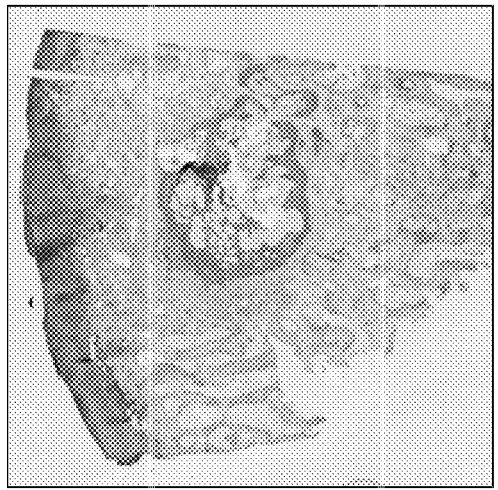
FIGS. 17a-d are longitudinal histological sections of the 6-mm osteochondral defects 4 months following implantation stained for Type II collagen using monoclonal antibodies. The defects are either left empty (FIG. 17a empty control) or treated with hydrogels of denatured PEGylated fibrinogen (FIGS. 17b-d) with different concentrations of PEG and fibrinogen in each treatment. Histology is shown for treatments with (FIG. 17b) 150:1 molar ratio of PEG to fibrinogen, (FIG. 17c) 200:1 molar ratio of PEG to fibrinogen, and (FIG. 17d) 350:1 molar ratio PEG to fibrinogen in the defect site. All treated defects showed new cartilage staining positive for collagen type II (brown color), compared to new bone which does not stain positive.
Figure 17D:
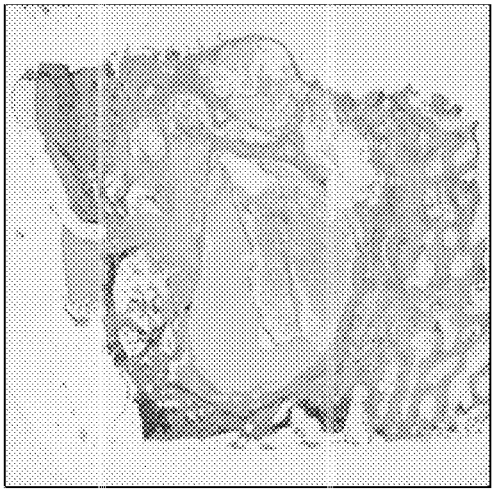
Figure 17A:
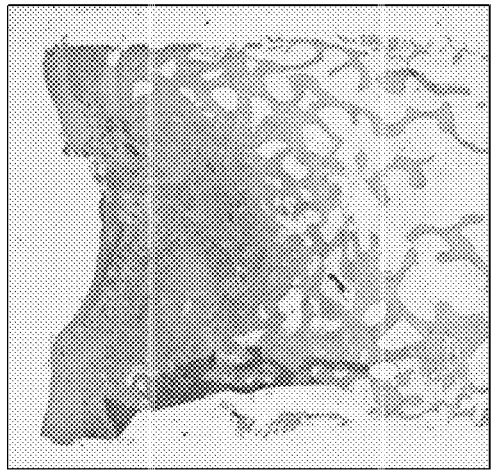
Figure 17C:
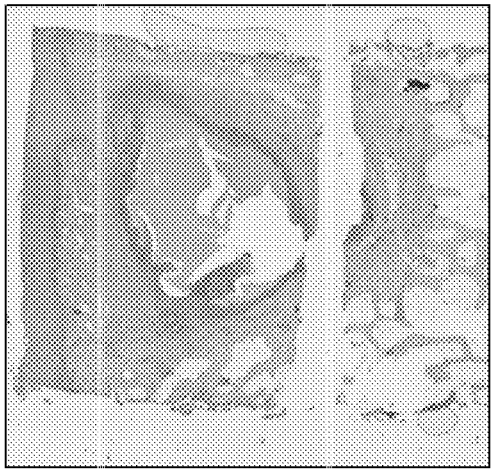

Histological evaluation of these defects revealed extensive new cartilage formation in the defect region, alongside new bone formation around the eroding implant (FIGS. 14b-d). Empty defects exhibited fibrocartilage and excessive scar tissue formation (FIG. 14a). The extent of released PEGylated degradation products and subsequent erosion of the hydrogel implant was dependent on the ratio of PEG to fibrinogen; hydrogels with more PEG exhibited slower erosion and slower release of the therapeutic PEGylated fibrinogen degradation products. FIGS. 14a-d summarizes the relationship between the molar ratio of the PEG to fibrinogen and the erosion patterns of the hydrogel implant. Further histological staining of the sections using stains for type I collagen (FIG. 15a-d), proteoglycans (FIG. 16a-d), and type II collagen (FIG. 17a-d) showed characteristic staining of articular (hyaline) cartilage above the newly formed boney bridge overtop the eroding implant. Type I collagen staining was performed (FIG. 15a-d) to verify new bone formation in the site of the defect, around the eroding implant. Proteoglycan staining was performed (FIG. 16a-d) to verify generation of hyaline cartilage in the treated defects (FIG. 16b-d) whereas control treated defects were not positive for proteoglycans (FIG. 16a). Type II collagen staining was performed (FIG. 17a-d) to confirm that the composition of the cartilage surface is consistent with the composition of hyaline cartilage; in those treated samples that were stained, the newly formed cartilage surface was found to be positive for type II collagen (FIG. 17b-d).

Osteogenesis and Chondrogenesis:

Newly formed cartilage and bone in the critical size defect was apparent in all three treatment conditions after 3-4 months (FIGS. 14b-d). On the other hand, control defects were filled with scar tissue and did not show any signs of chondrogenesis (FIG. 14a). It is suggested that the slow-released implants may be more effective in healing the injury based on the quality of the articular cartilage formed in the treated defect (FIGS. 19a-d). Similar with the bone study, it is clear that the PEGylated fibrinogen material is endowed with both inductive properties for bone and cartilage repair and that the macrophages that erode the denatured PEGylated fibrinogen containing matrix slowly release osteoinductive denatured PEGylated fibrinogen degradation products to act as an eroding front for osteoneogenesis and chondrogenesis to occur in as much as the gels slowly give way for the newly generating bone and cartilage. Here again, it is important to note that we arbitrarily choose the composition of gel to coincide with the optimal degradation rate and healing kinetics in this type of injury. Consequently, the healing kinetics of this injury are such that it was possible to observe cartilage regeneration in all the three treatment conditions whereas the control group (empty defect) was clearly not capable of creating new cartilage. Even though these compositions were optimal for this type of injury in sheep, it is the ability to regulate the degradation and release of the PEGylated fibrinogen degradation products that affords this technology with the versatility for treating the same injury in humans.

Figure 18B:
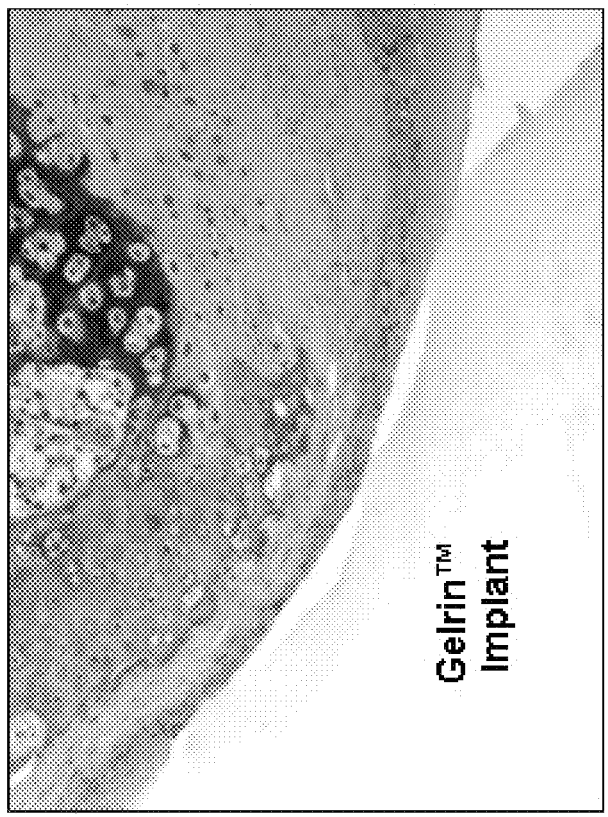
FIGS. 18a-b are histological sections of osteochondral defects treated with PEGylated fibrinogen implants shown at the implant-tissue interface after 4 months.
Figure 18A:
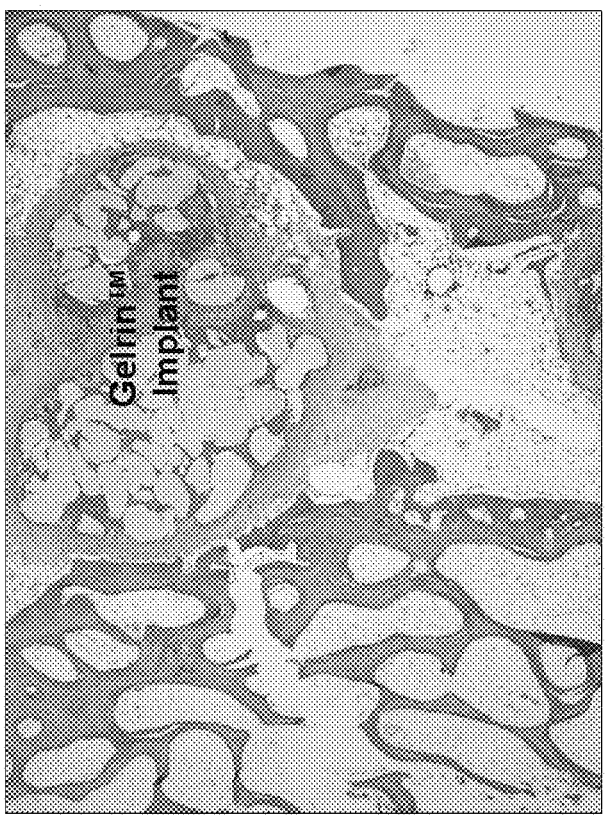

Fragments released from the PEG-fibrinogen hydrogel facilitated a prolonged osteogenic and chondrogenic response within the subchondrol lesion. As with the rat study above, a sustained release of the denatured PEGylated fibrinogen degradation products explain the extent of the oesteogenic and chondrogenic response in the treated animals. The observed chondrogenesis in particular is attributed to the released fragments of PEGylated fibrinogen degradation products and not to the intact matrix. A sustained presentation of mildly inductive PEGylated fibrinogen fragments could account for the prolonged chondrogenic response over the 4 months of the healing. This explanation is consistent with the fact that most of the regeneration of bone and cartilage in the treated defects occurs at least several hundred microns from the eroding surface of the hydrogels (FIGS. 18a-b), the latter being consistently surrounded by an inflammatory infiltrate.

It is particularly impressive to see the extent of the seamless integration between the margins of the defect and the newly formed cartilage in the treated animals (FIGS. 20a-f). In some cases, it was difficult to gauge where the original margins of the defect ended and the newly formed tissue began. Similarly, the newly formed bone was very well integrated with the surrounding existing bone tissue of the injury margins. This is an important indicator of the quality of the healing that is achievable by means of the PEGylated denatured fibrinogen degradation technology.

Conclusions:

Injecting implants that erode and release PEGylated denatured fibrinogen degradation products into an osteochondral defect site can promote the repair of the articular cartilage surface through induction and synchronized release of the inductive fibrinogen fragments.

Example 6

Controlling Three-Dimensional Neurite Outgrowth Using Peg-Fibrinogen Hydrogels

To test the potential of the PEG-fibrinogen scaffold material to facilitate nerve regeneration, a chicken embryo dorsal root ganglion (DRG) outgrowth model was used. In the initial stage of nerve regeneration fibrin provides Schwann cells environmental cues for proliferation, thus ensuring that there are enough cells to associate with the regenerating neurons. In the absence of fibrin, Schwann cells can then differentiate and re-myelinate the newly formed axons. Accordingly, this model implies that the untimely persistence of fibrin in the injury site can interfere with the delicate timing of the nerve regeneration process and disrupt the construction of functional nerve tissue. Therefore the ability to control the degradation and removal of the fibrin matrix is crucial for enabling successful nerve regeneration.

The synthetic PEG component provides the desired physical properties and controllable degradation characteristics. The natural fibrinogen component of the biosynthetic matrix supplies cues that regulate Schwann cell proliferation and migration and therefore will likely influence re-myelination of the regenerated axons. An additional advantage of the PEGylated fibrinogen approach is that it enables the control of the relative bioactivity of the fibrinogen degradation products based on the rationale that covalently bound PEG can decrease the accessibility to active sites on both intact and degraded fibrinogen molecule. Hence, a PEGylation strategy offers control over fibrinogen degradation, bioactivity, and molecular architecture of the nerve guidance conduit (NGC) cell ingrowth matrix.

In addition, the present inventor has shown that it is possible to control the biodegradation of the fibrinogen matrix by changing relative amounts of fibrinogen and PEG in such a system. To this end, Dikovsky et al. showed that increased PEG-DA concentrations in the PEGylated fibrinogen hydrogel decreased proteolytic susceptibility of the protein backbone and thus delayed the PEGylated fibrinogen biodegradation [Dikovsky D. et al. Biomaterials 2006; 27(8):1496-506]. The PEGylated fibrinogen system also presents additional advantages for nerve regeneration in that therapeutic growth factors can easily be encapsulated and enmeshed in the dense polymeric network of the hydrogel during the polymerization process. The encapsulation of factors for nerve regeneration could provide neuron-specific signals beyond the inherent biological and structural provisions of the PEGylated fibrinogen hydrogel network. One of the most vital neurotrophins in neuronal development and regeneration is nerve growth factor (NGF). Schwann cells produce NGF, a 26 kDa dimmer, in their immature phase during early development and after post-injury dedifferentiation in mature nerves. Accordingly, it is important that NGF be an integral part of the nerve guidance implant material.

Materials and Experimental Methods

Dorsal Root Ganglia Experiments:

DRGs were dissected from E9-E11 chicken embryos and collected in PBS with 1% penicillin-streptomycin (Biological industries, Kibbutz Beit Haemek, Israel). Fibroblast contamination of the DRGs was minimized by pre-plating the DRGs for one hour in MEM with Glutamax I medium (Gibco, Grand Island, N.Y., USA) containing 1% penicillin-streptomycin and 10% fetal calf serum (FCS) (Biological industries, Kibbutz Beit Haemek, Israel). The pre-plated DRGs were then physically removed from the culture dish and entrapped in hydrogel constructs prepared from a precursor solution of PEGylated fibrinogen (prepared as described in Example 1) and photoinitiator. Briefly, the precursor solution was mixed with 1% (v/v) photoinitiator stock solution made of 10% (w/v) Irgacure™ 2959 (Ciba Specialty Chemicals, Tarrytwon, N.Y.) in 70% ethanol and deionized water. The solution was then centrifuged at 14,000 RPM for 1 minute before being used to entrap the isolated DRGs. The entrapment procedure involved gently placing the intact DRGs into a 48-well plate containing the precursor solution. The 48-well plate was first pre-coated with 100 μl polymerized PEGylated fibrinogen in order to prevent cell growth on the bottom of the well. Each DRG was placed into 200 μl PEGylated fibrinogen solution and polymerized under a UV light (365 nm, 4-5 mW/cm$^2$) for 5 minutes. After hydrogel polymerization, the entrapped DRGs were visually inspected to ensure 3-D encapsulation in the biosynthetic matrix (FIGS. 25a-c). Culture medium was immediately added to the polymerized hydrogels (500 μl in each well) and changed every two days. The culture medium was comprised of MEM with Glutamax I medium containing 1% penicillin-streptomycin and 10% FCS. Unless otherwise indicated, the medium was supplemented with 50 ng/ml 2.5S mouse nerve growth factor (mNGF) (Alomone labs LTD., Jerusalem, Israel).

Quantitative Outgrowth Measurements:

Cellular outgrowth from the DRG into the transparent PEGylated fibrinogen hydrogel was recorded during the four-day duration of the experiment. Each DRG construct was documented with digital images taken daily using a Nikon TE2000 phase contrast microscope with a 4× objective and a digital CCD camera (Jenoptik, Germany). Quantitative neurite outgrowth measurements were obtained directly from the digital phase contrast micrographs using ImageJ software. Neurites, which can be identified by their characteristic sprouting morphology, were measured from the base (outer margin of the DRG) along their length and up to the tip. Up to a total of 80 measurements were made for each DRG construct, according to the ability to trace continuous neurites. The mean DRG neurite outgrowth was then calculated for each individual DRG construct by averaging the 80 measurements of each construct (n=1). The average neurite outgrowth for each treatment was calculated using the mean DRG neurite outgrowth data.

Histology and Immunofluorescence:

Preparation of the DRG specimens for histological and immunofluorescence evaluation involved fixation in 4% paraformaldehyde (Gadot, Haifa, Israel) for 20-30 min, PBS rinses, and overnight cryoprotection in a 30% sucrose solution (in PBS) at 4° C. Each fixed construct was then slow-frozen in Tissue-Tek® O.C.T Compound (Sakura Finetek, Torrance, Calif., USA) using liquid nitrogen cooled isopropanol (Gadot, Haifa, Israel). Frozen constructs were stored in a deep freezer (−80° C.) for up to three months. The specimens were sectioned orthogonally into 30-µm thick slices using a cryostat and mounted on Polysin™ slides (Menzel-Glaser, Braunschweig, Germany). Prior to staining, the slides were air dried at RT for 2 hours and stored at −20° C. Hematoxylin and Eosin (H&E) staining (Sigma, St. Louis, Mo., USA) was performed according to standard manufacturer's protocols.

Immunofluoerscence labeling of the 30-µm thick specimens involved treatment with 0.3% Triton® X-100 (Bio Lab LTD., Jerusalem, Israel) for 5 min at RT and incubation in blocking solution containing PBS and 1% glycine, 10% horse donor serum (HDS) (Biological industries, Kibbutz Beit Haemek, Israel) and 0.1% Triton® X-100 for 30 min at RT. The sections were double stained with primary antibodies against βIII-tubulin, (G712A, Promega, Madison, Wis., USA) and s100 (S2644, Sigma, St. Louis, Mo., USA). The primary antibodies were diluted in blocking solution (1:1000 dilution for βIII-tubulin and 1:200 dilution for s100) and incubated overnight at 4° C. in a humidity chamber. The sections were rinsed and incubated for 30 minutes at RT with fluorescently conjugated secondary antibodies, including 1:250 diluted goat anti-mouse Cy3 (Chemicon International, Temecula, Calif., USA) for βIII-tubulin and 1:300 diluted goat anti-rabbit FITC (Jackson Immunoresearch Laboratories INC., west Grove, Pa., USA) for s100. A nuclear counter-stain was incorporated directly into the secondary antibody staining solution using a 1:500 diluted DAPI stock solution (Sigma Aldrich, St. Louis, Mo., USA). Following incubation, sections were rinsed with PBS and mounted with FluoromountG (Southern Biotechnology Associates, INC., Birmingham, Ala., USA).

Statistical Analysis:

Statistical analysis was preformed on data sets from at least two independent experiments. Depending on the data set, treatments were compared by single-factor ANOVA, two-factor ANOVA, or paired student t-test. Statistical significance was accepted for $p<0.01$.

Experimental Results

DRG Outgrowth:

Tissue constructs were prepared by entrapping DRGs inside PEGylated fibrinogen hydrogels (FIGS. 21a-c) and cultivating them for up to one month in a $CO_2$ incubator. Cellular outgrowth from the DRG was visible in phase contrast micrographs and histological H&E sections (FIGS. 22a-d). Throughout the experiment, cells from the DRG invaded the PEGylated fibrinogen hydrogel and eventually occupied the entire gel (not shown). Phase contrast micrographs show the distinct spatial organization and orientation of the invading DRG cells into the PEGylated fibrinogen matrix after two days (FIG. 22a). A high magnification of this organization is shown in FIG. 22b, where long thin processes (neurites) extending out of the DRG are accompanied by non-neuronal cells (dark circular spots) that emerge from the DRG core and align along the neurite extensions. The non-neuronal outgrowth from DRGs (FIG. 22b, arrowhead) was shown to lag after neurite extensions (FIG. 22b, arrow). Histological cross-sections (30 µm) of the DRG constructs following four days of culture stained with H&E showed similar cellular invasion characteristics (FIGS. 22c-d).

The arrangement of non-neuronal (glial) cells invading from the DRG and aligning with the neurites resembled the in vivo spatial organization of neurons and their associated Schwann cells. In order to identify the different invading DRG cells in these experiments, neurites and Schwann cells were both labeled with neuronal and glial immunofluorescent markers. Immuno-detection in 30 µm thick cross-sections of the DRG constructs was preformed with the neuronal marker βIII-tubulin antibody and the Schwann cell marker s100 antibody. The labeling clearly shows extending neurites originating from the DRG into the matrix, and associated Schwann cells in close proximity to the invading neuronal cells (FIGS. 23a-c). Higher magnification images show the Schwann cells closely associated with the neurites to the extent that they align along with and adjacent to the βIII-tubulin positive extensions (FIGS. 23d-f). These results were well correlated to observations of the DRG cells inside the hydrogel as observed by phase contrast microscopy (FIGS. 22a-b).

Nerve Growth Factor Treatments:

Experiments to examine the influence of NGF in the culture medium versus encapsulated in the hydrogel during its formation were performed with DRG outgrowth constructs. Three treatment conditions were compared: a treatment using no NGF (NO-NGF), a treatment using free-soluble NGF in the culture medium (FS-NGF), and a treatment with enmeshed NGF in the hydrogel network (EN-NGF). Two independent experiments in each treatment condition were preformed for a total of six repeats using two different batches of PEGylated fibrinogen precursors. The constructs were cultured for four days and imaged daily to measure the progress of 3-D cell outgrowth from the DRGs into the hydrogel network. Based on results from the phase contrast micrographs (data not shown), the free-soluble and enmeshed NGF (FS-NGF and EN-NGF) facilitated outgrowth of both non-neuronal cells and neurites into the hydrogel as compared to NGF-deprived constructs (NO-NGF). In the absence of NGF, there was no observable outgrowth of neurites and only partial outgrowth of non-neuronal cells, which were most likely Schwann cells or fibroblasts. Immunohistochemistry confirms the observations of phase contrast microscopy in that βIII-tubulin and s100 positive cells were present in NGF treatments (FS-NGF and EN-NGF) but only s100 positive cells were seen in the NGF-deprived treatment (NO-NGF) (FIGS. 24a-c). Based on these qualitative data, it is difficult to conclude if there are significant differences in 3-D DRG outgrowth between the free soluble and enmeshed NGF; both free soluble NGF (FS-NGF) and enmeshed NGF (EN-NGF) treatments showed a similar labeling pattern.

In order to further differentiate between the free soluble and enmeshed NGF treatments, quantitative outgrowth experiments were performed. Using digital image processing, the distance of neurite outgrowth was measured in DRG constructs that were cultured with free soluble NGF (FS-NGF) or enmeshed NGF (EN-NGF). FIG. 28d shows that there was little difference between the two treatment conditions at any time during the culture period ($p>0.35$, n=6). In both free soluble and enmeshed NGF, there was a rapid increase in neurite outgrowth over the course of the four-day experiment ($P<0.01$, n=6), with a mean neurite length reaching 719.9 µm and 701.2 µm for FS-NGF and EN-NGF treatments, respectively after four days.

Cellular Outgrowth and Hydrogel Biodegradation:

Alterations to the biodegradation properties of the fibrinogen backbone of the hydrogel matrix can also influence the DRG cellular outgrowth characteristics, particularly as related to the relative invasion of Schwann cells and neurites. Experiments were performed to assess the ability to regulate the outgrowth kinetics using different compositions of the matrix (relative amount of PEG and fibrinogen) based on the rationale that the proteolytic resistance of the fibrinogen matrix will increase with increasing concentrations of PEG. Consequently, the PEGylated fibrinogen hydrogels also become more cross-linked with additional PEG, thereby changing the mesh size, hydration and mechanical properties of the matrix. Four different compositions of PEG to fibrinogen were tested, including: 30:1, 60:1, 120:1, and 180:1 (PEG:fibrinogen). It is important to note that the composition of the constructs in each treatment level was such that the pure PEGylated fibrinogen solution (30:1 treatment) was modified with additional unreacted PEG-DA before the UV polymerization step. Two independent experiments in each treatment level were preformed for a total of nine repeats using two different batches of pure PEGylated fibrinogen precursors.

Overall, the extent of cellular outgrowth from the DRG into the matrix was decreased with addition of higher concentrations of PEG-DA in the hydrogel matrix (FIGS. 25a-p). The lag between neurites and glial cells was visibly reduced with the addition of higher concentrations of PEG-DA (FIGS. 25q-t). A summary of the neurite outgrowth kinetics data with the different concentrations of PEG is summarized in FIG. 25u. Statistical analysis of the kinetics data (2-factor ANOVA) revealed that outgrowth steadily increased with culture time ($p<0.01$, $n=9$) and that higher concentrations of PEG slowed down the cellular invasion ($p<0.01$, $n=9$). In particular, constructs made with high concentrations of PEG-DA (120:1 and 180:1) delayed neurite outgrowth significantly from day 2 of culture when compared to constructs made with lower concentrations of PEG (30:1 and 60:1). Neurite outgrowth in the 180:1 hydrogels exhibited slowest outgrowth kinetics of all treatment levels, and reached a mean neurite length of 201.6 µm following four days of culture. Constructs made with 120:1 exhibited moderate neurite outgrowth rate and reached a mean neurite length of 490.8 µm following four days. There was no significant difference in neurite outgrowth between the 30:1 and 60:1 treatment levels ($p>0.50$, $n=9$); in both cases, outgrowth progressed most rapidly and reached a mean neurite length of 807.8 µm and 850.6 µm, respectively following four days of culture.

Fibrinogen and DRG Cellular Outgrowth:

The importance of the fibrinogen backbone in enabling cellular outgrowth from the DRG into the PEGylated fibrinogen matrix was investigated using PEG-only hydrogels as controls. DRG constructs were made of 10% PEG-DA without fibrinogen and compared to constructs made with PEGylated fibrinogen. The constructs were cultured for three days and cellular outgrowth was documented on the third day of culture. FIG. 26a shows that without fibrinogen, very few neurites extend out of the DRG and outgrowth of non-neuronal cells, including Schwann cells, was not observed. In contrast, fibrinogen containing hydrogels exhibit massive DRG outgrowth, including neurite and Schwann cell invasion, following three days of culture (FIG. 26b). These results demonstrate fibrinogen's role in permitting DRG outgrowth that includes proteolytic susceptibility, inductive and conductive environmental cues which may be crucial for functional peripheral nerve regeneration. Consequently, neuronal outgrowth was practically eliminated even in the PEGylated fibrinogen hydrogels when DRG cultures were deprived of NGF (NO-NGF), whereas other cell types (including Schwann cells) are observed invading the hydrogel (FIG. 26c).

Analysis and Discussion

Peripheral nerve regeneration is a complex, highly regulated process which requires specific environmental cues that are provided by the extracellular matrix (ECM) and the tight bi-directional communication between regenerating axons and their associated Schwann cells. Many peripheral nerve regeneration strategies using NGCs have been designed to provide the optimal milieu for PNS regeneration, using natural or synthetic materials and different growth factor delivery strategies. Because NGCs have yet to achieve the efficacy of the nerve autografts, alternative approaches are sought that can leverage the natural healing mechanisms of peripheral nerve repair following moderate injury. To this end, the PEGylated protein hydrogels of the present invention can serve as a template for nerve regeneration which combines the paracrine effects of fibrin(ogen) and the control over biodegradation and bioactivity afforded by the PEGylation paradigm.

The experiments described hereinabove support a potential NGC biomaterial system based on PEGylated fibrinogen hydrogels that maintain outgrowth of DRG cells. A 3-D hydrogel matrix composed of PEG and fibrinogen was used to encapsulate chicken embryo DRGs to form transparent constructs that enable straightforward monitoring of the DRG outgrowth (FIGS. 21a-c). Outgrowth of neurites and non-neuronal (glial) cells was observed from the DRG into the hydrogel (FIGS. 22a-d). Furthermore, in vivo like spatial organization of these cells was observed. Specifically, the long neurites were observed in close proximity to their associated glial cells. Using antibodies specific for βIII-tubulin and s100, it was shown that the s100-positive Schwann cells are highly associated with the radially extending βIII-tubulin positive neurites (FIG. 23a-f). These neuron-Schwann cell complexes enable the production and organization of myelin along the length of extending axons in order to provide rapid and efficient propagation of action potentials along axons. Consequently, this distinct spatial organization is a prerequisite for axonal myelination during the later phase of neuronal regeneration.

It is likely that DRG neurites and glial cells employ a proteolytic mechanism to invade the PEGylated fibrinogen hydrogel matrix in as much as the hydrogel is highly susceptible to proteases [Almany L, et al. Biomaterials 2005; 26(15):2467-77] and is otherwise too dense to permit cellular invasion in the absence of proteolysis. Because the fibrinogen backbone affords the biosynthetic hydrogel its biodegradability, it also provides a means of releasing cleaved fragments of fibrinogen from the matrix upon degradation. In this manner the kinetics of neurite and glial cell invasion as well as the bioactivity of the released fibrinogen fragments can be controlled by changing the relative amount of PEG and fibrinogen. Higher amounts of PEG reduce the susceptibility to proteolytic degradation of the fibrinogen backbone [Dikovsky D, et al, Biomaterials 2006; 27(8):1496-506] and presumably reduces the overall bioactivity of the degraded fibrinogen fragments that are released to the surrounding tissue [Hooftman G, et al. J Bioact Compat Polym 1996; 11:135-159]. Indeed, the addition of PEG to the biosynthetic hydrogel slows down the invasion of both Schwann cells and neurites from the DRG (FIGS. 25a-p). Furthermore, it appeared that in lower concentrations of PEG, the non-neuronal outgrowth from DRGs lagged behind the neurite extensions, whereas the higher concentrations of PEG minimized this lag (FIGS. 25q-t).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A scaffold comprising a plurality of denatured fibrinogen molecules and a plurality of crosslinked synthetic polymers, each of said denatured fibrinogen molecules being covalently attached to at least two of said crosslinked synthetic polymers, wherein said synthetic polymers are crosslinked between said polymers.

2. The scaffold of claim 1, wherein said scaffold is biodegradable.

3. The scaffold of claim 1, wherein said synthetic polymer is selected from the group consisting of polyethylene glycol (PEG), Hydroxyapatite/polycaprolactone (HA/PLC), polyglycolic acid (PGA), Poly-L-lactic acid (PLLA), Polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and nonbiodegradable polytetrafluoroethylene (PTFE).

4. The scaffold of claim 1, wherein said synthetic polymer is PEG.

5. The scaffold of claim 1, wherein said fibrinogen is denatured using a denaturing agent.

6. The scaffold of claim 1, further comprising a growth factor.

7. The scaffold of claim 6, wherein said growth factor is NGF.

8. The scaffold of claim 1, wherein said fibrinogen is whole fibrinogen or fragmented fibrinogen.

9. The scaffold of claim 1, which does not comprise more than 10% of said synthetic polymer unattached to said denatured fibrinogen.

10. A hydrogel formed from the scaffold of claim 1.

11. The hydrogel of claim 10, wherein said naturally occurring protein is whole fibrinogen and whereas a concentration of said units in said hydrogel is selected from a range of 0.5-35%.

12. The hydrogel of claim 10, wherein said fibrinogen is fragmented fibrinogen and whereas a concentration of said units in said hydrogel is selected from a range of 0.5-35%.

13. The hydrogel of claim 11, wherein modulus of elasticity of said hydrogel is in a range of 0.02-0.11 kPa for 10-20% polymer.

14. The hydrogel of claim 12, wherein modulus of elasticity of said hydrogel is in a range of 0.01-0.07 kPa for 10-20% polymer.

15. The scaffold of claim 1, obtainable by:
(a) obtaining a composition comprising a plurality of precursor molecules, each of said precursor molecules comprising fibrinogen and at least two synthetic polymers covalently attached to said fibrinogen, each of said at least two synthetic polymers having a functional group which is capable of cross-linking with a functional group of the synthetic polymer of at least one other of said precursor molecules, said composition further comprising the unconjugated form of said synthetic polymer;

(b) removing the unconjugated form of said synthetic polymer; and subsequently (c) crosslinking said plurality of precursor molecules.

16. The scaffold of claim 5, wherein said denaturing agent is selected from the group consisting of urea and guanidine chloride.

\* \* \* \* \*